US009943725B2

(12) United States Patent
Todd et al.

(10) Patent No.: US 9,943,725 B2
(45) Date of Patent: Apr. 17, 2018

(54) EXERCISE BALANCE TRAINER

(71) Applicant: InertiaCore Training Systems LLC, Baldwinsville, NY (US)

(72) Inventors: Terri Todd, Chittenango, NY (US); Byron Tietjen, Baldwinsville, NY (US)

(73) Assignee: InertiaCore Training Systems LLC, Baldwinsville, NY (US)

( * ) Notice: Subject to any disclaimer, the term of this patent is extended or adjusted under 35 U.S.C. 154(b) by 0 days.

(21) Appl. No.: 15/347,943

(22) Filed: Nov. 10, 2016

(65) Prior Publication Data

US 2017/0056728 A1    Mar. 2, 2017

Related U.S. Application Data

(63) Continuation-in-part of application No. 14/173,606, filed on Feb. 5, 2014, now Pat. No. 9,616,285, which
(Continued)

(51) Int. Cl.
*A63B 21/08*    (2006.01)
*A63B 26/00*    (2006.01)
(Continued)

(52) U.S. Cl.
CPC .......... *A63B 26/003* (2013.01); *A61B 5/1118* (2013.01); *A61B 5/486* (2013.01);
(Continued)

(58) Field of Classification Search
CPC ........ A63B 21/1492; A63B 2208/0233; A63B 23/0211; A63B 21/0004; A63B 21/00116;
(Continued)

(56) References Cited

U.S. PATENT DOCUMENTS

| 478,166 | A | * | 7/1892 | Madsen | ................. | A63B 23/08 482/146 |
| 2,719,571 | A | * | 10/1955 | Taylor | ................... | A47C 9/002 248/371 |

(Continued)

OTHER PUBLICATIONS

SAE, J684 Trailer Couplings, Hitches, and Safety Chains—Automotive Type, Guidelines Fifth Revision, Aug. 2000, SAE International, Warrendale, PA.
(Continued)

*Primary Examiner* — Joshua Lee
(74) *Attorney, Agent, or Firm* — Craige Thompson; Thompson Patent Law

(57) ABSTRACT

Apparatus and associated methods relate to a balance exercise training equipment having a planar platform with a ballast assembly that lowers its center of mass below a ball-and-socket joint. In an illustrative example, the planar platform may couple to a support assembly through the ball and socket joint to pivot and rotate relative to the support assembly. The ballast assembly may include laterally extending members to releasably receive and retain ballast plates. In response to the laterally extending members receiving and retaining ballast plates, the center of mass may descend below a pivot point of the ball-and-socket joint. In a mount or dismount mode, a locking mechanism may lock the planar platform in a predetermined position to facilitate mounting and dismounting onto the planar platform. Advantageously, a user may adjust the center of mass in accordance with a user's skill level or exercise preference.

18 Claims, 18 Drawing Sheets

Related U.S. Application Data is a continuation-in-part of application No. 13/685,968, filed on Nov. 27, 2012.

(60) Provisional application No. 61/911,344, filed on Dec. 3, 2013, provisional application No. 61/760,832, filed on Feb. 5, 2013.

(51) Int. Cl.

| | |
|---|---|
| *A63B 23/02* | (2006.01) |
| *A63B 21/06* | (2006.01) |
| *F16B 7/10* | (2006.01) |
| *A61B 5/00* | (2006.01) |
| *A61B 5/11* | (2006.01) |
| A63B 69/06 | (2006.01) |
| A63B 21/00 | (2006.01) |
| A63B 21/055 | (2006.01) |
| A63B 71/00 | (2006.01) |
| A63B 71/06 | (2006.01) |
| A63B 21/02 | (2006.01) |
| A63B 23/035 | (2006.01) |
| A63B 69/00 | (2006.01) |
| A63B 21/072 | (2006.01) |
| A63B 23/00 | (2006.01) |
| A63B 22/18 | (2006.01) |
| A63B 23/12 | (2006.01) |

(52) U.S. Cl.
CPC ...... *A61B 5/6895* (2013.01); *A63B 21/00069* (2013.01); *A63B 21/0615* (2013.01); *A63B 21/4033* (2015.10); *A63B 21/4047* (2015.10); *A63B 23/0222* (2013.01); *A63B 23/03525* (2013.01); *F16B 7/10* (2013.01); *A61B 5/6898* (2013.01); *A61B 2562/0219* (2013.01); *A63B 21/00065* (2013.01); *A63B 21/023* (2013.01); *A63B 21/0552* (2013.01); *A63B 21/072* (2013.01); *A63B 21/4034* (2015.10); *A63B 21/4035* (2015.10); *A63B 21/4049* (2015.10); *A63B 22/18* (2013.01); *A63B 23/0216* (2013.01); *A63B 23/03533* (2013.01); *A63B 23/1209* (2013.01); *A63B 69/0064* (2013.01); *A63B 69/06* (2013.01); *A63B 71/0054* (2013.01); *A63B 71/0622* (2013.01); *A63B 2023/003* (2013.01); *A63B 2069/068* (2013.01); *A63B 2071/0018* (2013.01); *A63B 2071/0063* (2013.01); *A63B 2071/0625* (2013.01); *A63B 2071/0655* (2013.01); *A63B 2071/0694* (2013.01); *A63B 2208/0204* (2013.01); *A63B 2208/0228* (2013.01); *A63B 2208/0233* (2013.01); *A63B 2220/10* (2013.01); *A63B 2220/13* (2013.01); *A63B 2220/17* (2013.01); *A63B 2220/24* (2013.01); *A63B 2220/30* (2013.01); *A63B 2220/40* (2013.01); *A63B 2220/51* (2013.01); *A63B 2220/803* (2013.01); *A63B 2225/09* (2013.01); *A63B 2225/093* (2013.01); *A63B 2230/01* (2013.01); *A63B 2230/75* (2013.01)

(58) Field of Classification Search
CPC ... A63B 21/0615; A63B 22/18; A63B 22/205; A63B 23/0216; A63B 23/0227; A63B 23/03583; A63B 21/00069; A63B 21/4033; A63B 21/4047; A63B 21/4049; A63B 21/4034; A63B 21/072; A63B 21/00065; A63B 21/023; A63B 21/0552; A63B 21/4035; A63B 22/14; A63B 22/16; A63B 23/03525; A63B 23/0222; A63B 23/1209; A63B 23/03533; A63B 2023/003; A63B 26/00; A63B 26/003; A63B 69/0064; A63B 69/06; A63B 2069/068; A63B 71/0622; A63B 71/0054; A63B 2071/0655; A63B 2071/0694; A63B 2071/0625; A63B 2071/0063; A63B 2208/0228; A63B 2208/0204; A63B 2220/803; A63B 2220/13; A63B 2220/10; A63B 2220/30; A63B 2220/24; A63B 2220/51; A63B 2220/40; A63B 2220/17; A63B 2225/093; A63B 2225/094; A63B 2230/01; A63B 2230/75; A61B 5/486; A61B 5/1118; A61B 5/6895; A61B 5/6898; A61B 2562/0219; F16B 7/10
USPC ...... 482/44–51, 72, 77–80, 92–98, 100–101, 482/110, 131–140, 143, 145–148; 297/195.1, 215.13–215.15, 258.1–272.4, 297/311–344.26; 472/95–97, 100, 102, 472/135; 434/247
See application file for complete search history.

(56) References Cited

U.S. PATENT DOCUMENTS

| | | | | |
|---|---|---|---|---|
| 4,186,920 A | * | 2/1980 | Fiore | A63B 22/18 403/138 |
| 4,605,220 A | * | 8/1986 | Troxel | A63B 23/08 482/112 |
| 4,605,334 A | * | 8/1986 | Kalvatn | A47C 9/002 248/182.1 |
| 4,641,833 A | * | 2/1987 | Trethewey | A63B 22/0076 482/114 |
| 5,385,154 A | * | 1/1995 | Fuhrman | A47C 15/008 128/845 |
| 5,728,049 A | * | 3/1998 | Alberts | A47C 9/002 297/314 |
| 6,022,303 A | * | 2/2000 | Abdo | A63B 23/0211 482/121 |
| 6,053,578 A | * | 4/2000 | van Hekken | A47C 1/03 297/411.35 |
| 6,264,588 B1 | * | 7/2001 | Ellis | A63B 21/068 482/100 |
| 6,379,289 B1 | * | 4/2002 | Gossie | A63B 21/055 482/138 |
| 6,485,398 B1 | * | 11/2002 | Kreft | A63B 23/03575 482/147 |
| RE38,057 E | * | 4/2003 | Pandozy | A63B 21/0615 482/137 |
| 6,666,802 B1 | * | 12/2003 | Rasmussen | A63B 21/0608 482/140 |
| 7,476,188 B2 | * | 1/2009 | Perez, Jr. | A63B 23/0211 472/103 |
| 7,594,881 B2 | * | 9/2009 | Shifferaw | A63B 21/0615 482/108 |
| 7,892,154 B1 | * | 2/2011 | Alexa | A63B 21/0083 482/112 |
| 8,172,732 B1 | * | 5/2012 | Webber | A63B 21/0615 482/140 |
| 2003/0139268 A1 | * | 7/2003 | Chen | A63B 22/18 482/146 |
| 2005/0101460 A1 | * | 5/2005 | Lobban | A63B 23/0211 482/140 |
| 2009/0230743 A1 | * | 9/2009 | Derakhshan | A47C 9/002 297/329 |
| 2010/0009818 A1 | * | 1/2010 | Simonson | A63B 21/0615 482/97 |
| 2011/0039669 A1 | * | 2/2011 | Stewart | A63B 21/015 482/146 |
| 2011/0301002 A1 | * | 12/2011 | Sebastian | A63B 21/068 482/140 |

(56) References Cited

U.S. PATENT DOCUMENTS

2012/0065036 A1\* 3/2012 Abercrombie, Jr. ... A61H 1/008
482/139

OTHER PUBLICATIONS

Kale, A., Acar, E., Haftka, R., and Stroud, W.J., Why are Airplanes so Safe Structurally?, 45th AIAA SSD&M Conference, Apr. 2004, AIAA, Palm Springs, CA.

Cautino, S., Cohen, G., Colella, J., Wilson, A., and Zankowsky, D., Biometrics: Kayak Exercise Machine, Dec. 2007, Northeastern University, Boston, MA.

\* cited by examiner

EXERCISE BALANCE TRAINER

CROSS-REFERENCE TO RELATED CASES

This application is a Continuation-in-part of U.S. application Ser. No. 14/173,606 entitled "Core Exercise Apparatus and Methods," filed by Terri Todd, et al., on Feb. 5, 2014, which claims the benefit of U.S. Provisional Application Ser. No. 61/911,344 entitled "InertiaCore Board Trainer," filed by Terri Todd, et al., on Dec. 3, 2013, and also claims the benefit of U.S. Provisional Application Ser. No. 61/760,832 entitled "Core Exercise Apparatus and Methods," filed by Byron Tietjen, et al., on Feb. 5, 2013, and is also a Continuation-in-part of U.S. application Ser. No. 13/685,968 entitled "Core Exercise Apparatus and Methods," filed by Terri Todd, et al., on Nov. 27, 2012.

This application incorporates the entire contents of the foregoing application(s) herein by reference.

SUMMARY OF ILLUSTRATIVE EMBODIMENTS

Apparatus and associated methods relate to a balance exercise training equipment having a planar platform with a ballast assembly that lowers its center of mass below a ball-and-socket joint. In an illustrative example, the planar platform may couple to a support assembly through the ball and socket joint to pivot and rotate relative to the support assembly. The ballast assembly may include laterally extending members to releasably receive and retain ballast plates. In response to the laterally extending members receiving and retaining ballast plates, the center of mass may descend below a pivot point of the ball-and-socket joint. In a mount or dismount mode, a locking mechanism may lock the planar platform in a predetermined position to facilitate mounting and dismounting onto the planar platform. Advantageously, a user may adjust the center of mass in accordance with a user's skill level or exercise preference.

A dual-mode exercise apparatus may include an articulating arm assembly coupled through a joint to a support assembly. In an illustrative embodiment, the arm assembly may include a seat centrally mounted above a ball-and-socket joint and a stabilizer member for the hands and/or feet of the user. In a first mode of operation a user sits on the seat and uses his or her core muscles to articulate the seat on the ball-and-socket joint against the resistance provided by, for instance, weights mounted on distal portions of the arm assembly. In certain embodiments the apparatus may further provide a second mode of operation which simulates rowing a kayak. In a corresponding illustrative embodiment, a user sits in a second seat positioned rearward of the arm assembly and the arm assembly includes handle members. In operation, the user articulates the handles in a manner akin to rowing a kayak.

The details of one or more implementations are set forth in the accompanying drawing and description below. Other features, objects, and advantages will be apparent from the description and drawings, and from the claims.

BRIEF DESCRIPTION OF FIGURES

Like reference symbols in various drawing indicate like elements.

DETAILED DESCRIPTION OF ILLUSTRATIVE IMPLEMENTATIONS

Figure 1:
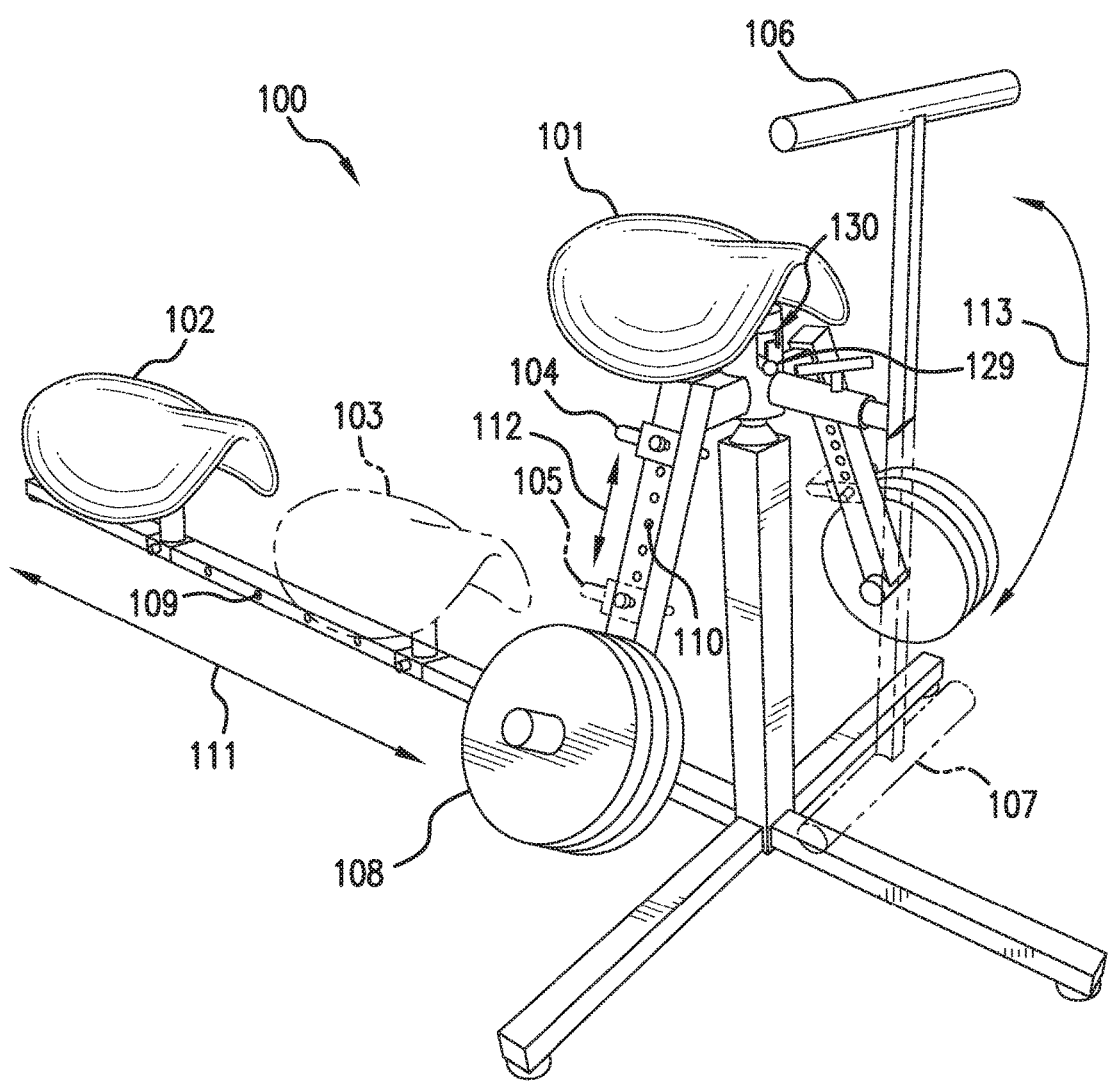
FIG. 1 is a perspective view of an illustrative core training apparatus.

FIG. 1 is a perspective view of an illustrative core training apparatus. FIG. 1 depicts a core training apparatus 100 which includes a support base that includes laterally extending support arms. The rearwardly extending arm is longer than the remaining three arms and slidably engages seat 102 which is secured in a desired position along the rearwardly extending arm with a pin that mates with one of a number of receiving apertures 109 located along the rearwardly extending arm. The seat 102 can be moved as shown by arrow 111 into various positions (e.g., as depicted in broken lines by a seat 103) along the rearwardly extending arm defined by pin receiving holes 109.

The support base also includes a vertically extending member which includes a ball member akin to that conventionally used as vehicular trailer hitches. A top that ball member is mounted a center post which includes a seat 101 opposite a socket member with a recess into which the ball is received. In certain embodiments, the socket member has one or more inwardly projecting locking mechanisms such as set screws which prevent the socket from lifting off of the ball. In the depicted example, the center post includes a locking pin 129 extending radially through a slot 130 in the center post. Examples of locking pin mechanisms are described in further detail with reference, for example, to at least FIG. 6. As depicted here, the locking pin 129 is in a lower position, which may correspond to the center post being in a locked state to prevent movement of the center post with respect to the ball. This locked state may provide, in some embodiments, a stable seat 101, for example, when a user mounts or dismounts from the seat 101.

Extending forwardly from the center post is a member that supports a handlebar/footrest 106. As shown by arrow 113 the handlebar/footrest 106 can articulate between an upper position in which the member serves as a handlebar and a lower position (e.g., as depicted in broken lines in the position as a footrest 107) in which the member serves as a footrest. In the depicted example, the handlebar/footrest 106 is locked into the desired position with a spring-loaded reciprocating pin.

Extending laterally from the center post are downwardly projecting arms which have handles 104 slideably mounted thereto. The handles 104 can be moved as shown by arrow 112 into various positions (e.g., as depicted in broken lines by handles 105) along the arms defined by pin receiving holes 110. At the distal (lower) ends of the downwardly projecting arms are ballast holding posts that project perpendicularly and laterally from the arms. The posts are configured to receive plates 108 that provide weight which is subject substantially to gravitational and inertial forces. In operation, the user may perform static and/or dynamic exercises by generating forces that overcome resistance associated with the gravitational and/or inertial forces on the ballast(s), such as the plates 108, for example.

Figure 2:
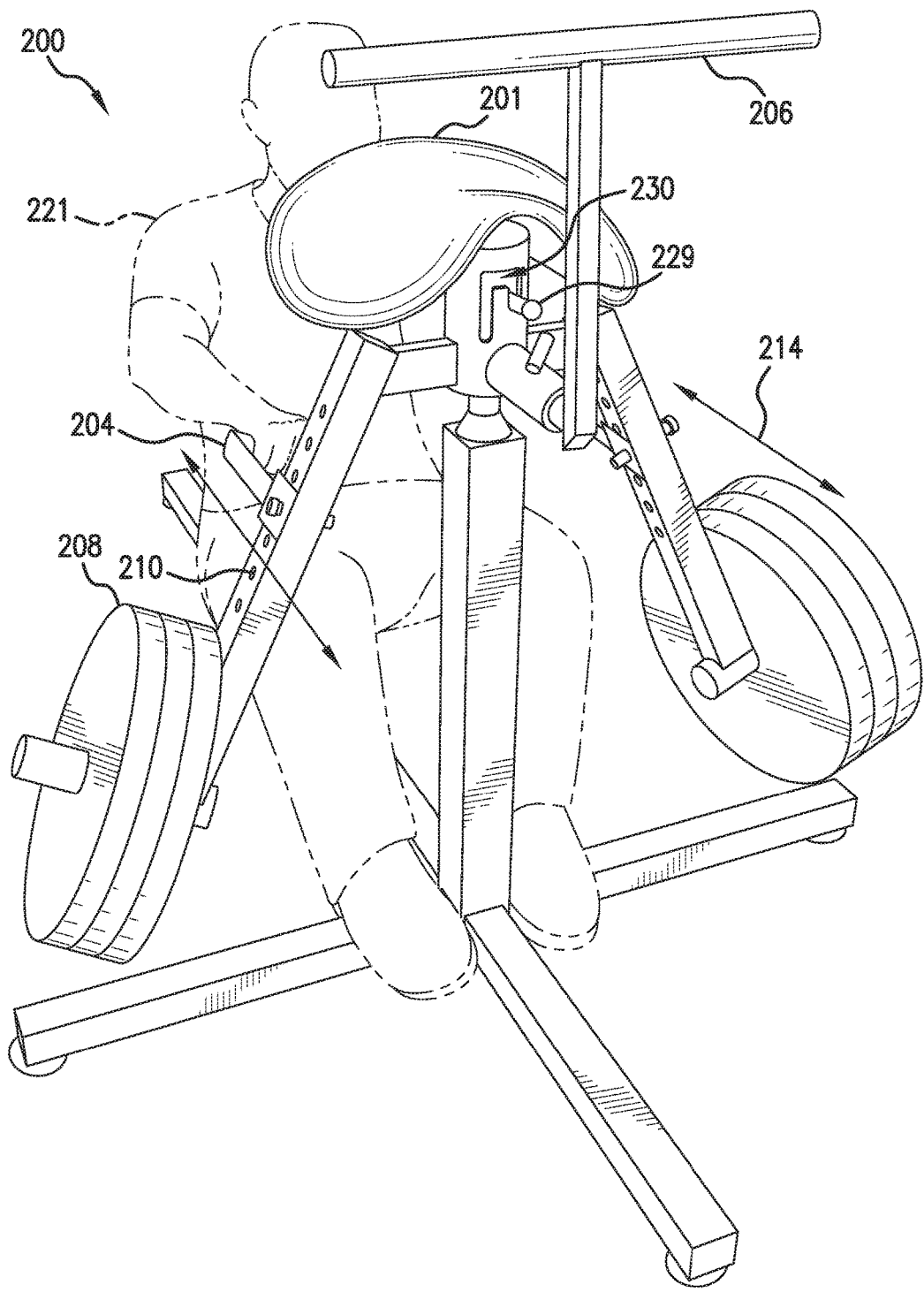
FIG. 2 is a perspective view of the illustrative core training apparatus which depicts a first operational mode.

FIG. 2 is a perspective view of the illustrative core training apparatus which depicts a first operational mode. As depicted, FIG. 2 shows an operational mode in which a user 221 performs a rowing exercise. The user 221 sits on the rearwardly extending arm and places his hands on the handles 204 and pulls one back while permitting the other to move forward in a motion similar to rowing a kayak with a dual-ended paddle. Viewed from the sides, the handles 204 progress through an oval-shaped range of motion. In other exercises the handles 204 may be articulated horizontally back and forth as shown by arrows 214. The handles 204 may be positioned at different heights to alter the difficulty, the range of motion and the muscles exercised. Examples of illustrative motion trajectories are described in further detail with reference, for example, to FIG. 5.

In the depicted example, the center post includes a locking pin 229 extending radially through a slot 230 in the center post. As depicted here, the locking pin 129 is in a raised position, which may correspond to the center post being in an unlocked state to permit movement of the center post with respect to the ball. This unlocked state may provide, in some embodiments, an articulating assembly coupled to the center post rotatably supported by the ball, for example, responsive to user applying dynamic forces via the handles 204, for example. In various embodiments, the seat 201 remains fixed when locked by the locking pin 229, and otherwise the seat 201 is able to move freely subject primarily to gravitational and inertial forces on the ballast 208.

Figure 3A:
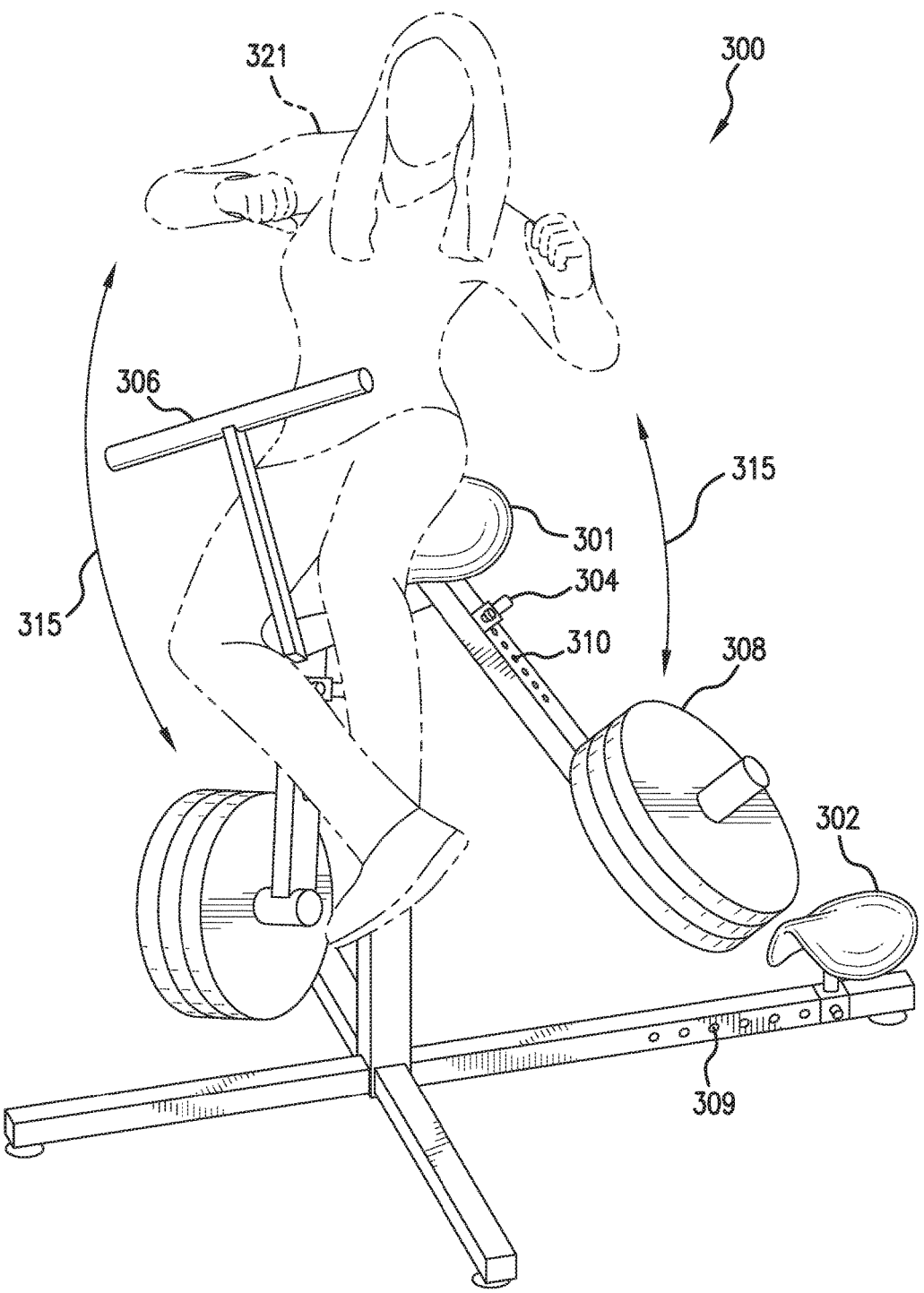
FIG. 3A is a perspective view of the illustrative core training apparatus which depicts a second operational mode.
Figure 3B:
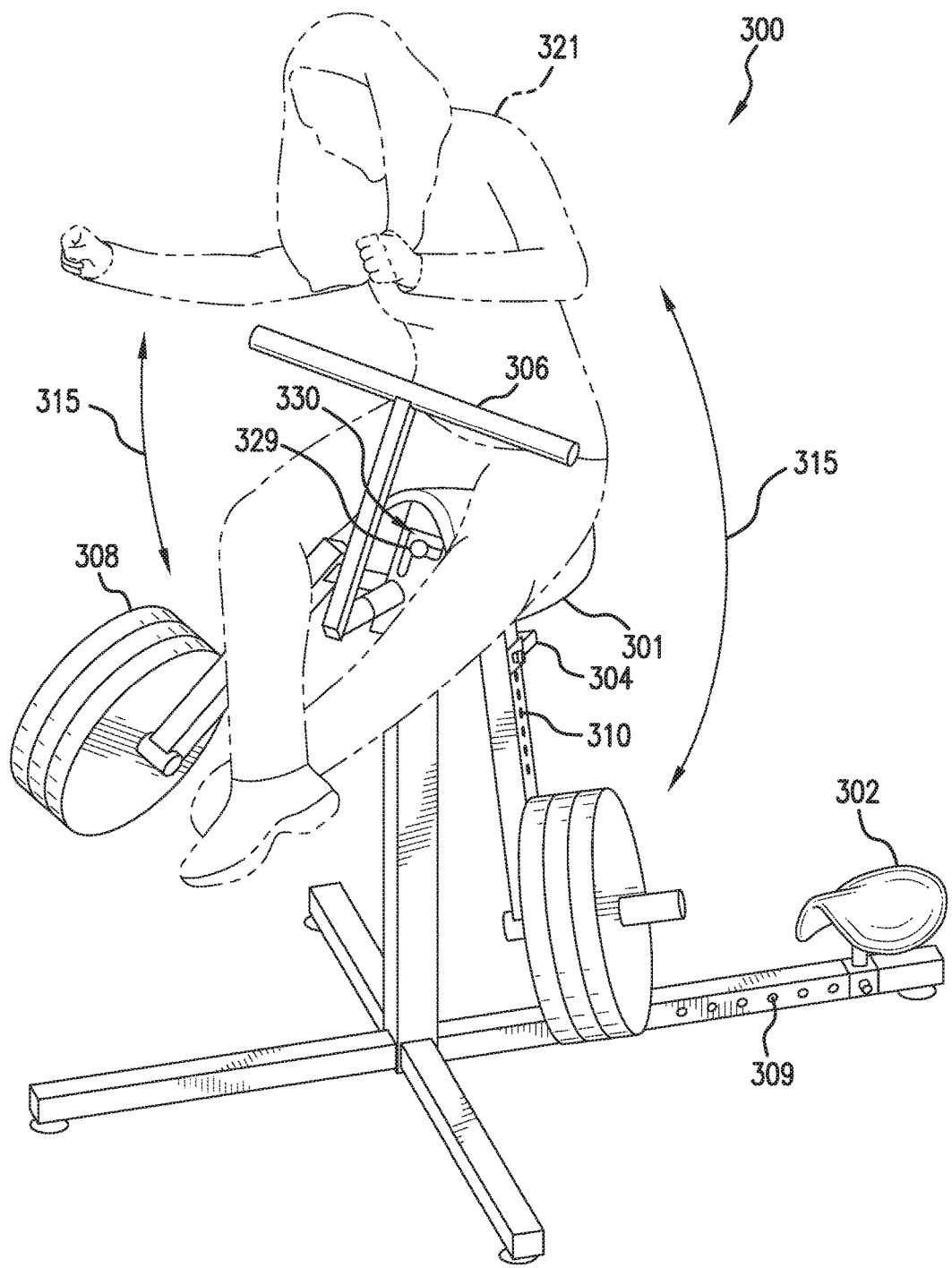
FIG. 3B is a perspective view of the illustrative core training apparatus which further depicts the second operational mode.

FIGS. 3A-3B show another operational mode in which a user sits atop the seat 301 and articulates the arm assembly through use of her core muscles. In this embodiment, the handlebar/footrest 306 is secured into an upper position. The user pivots her upper torso relative to her lower torso in order to articulate the apparatus in a side-to-side motion illustrated by arrows 315. FIG. 3A illustrates a point in the range of motion in which the apparatus is fully articulated to the user's left hand side. FIG. 3B illustrates a point in the range of motion in which the apparatus is articulated to the user's right-hand side.

Figure 4A:
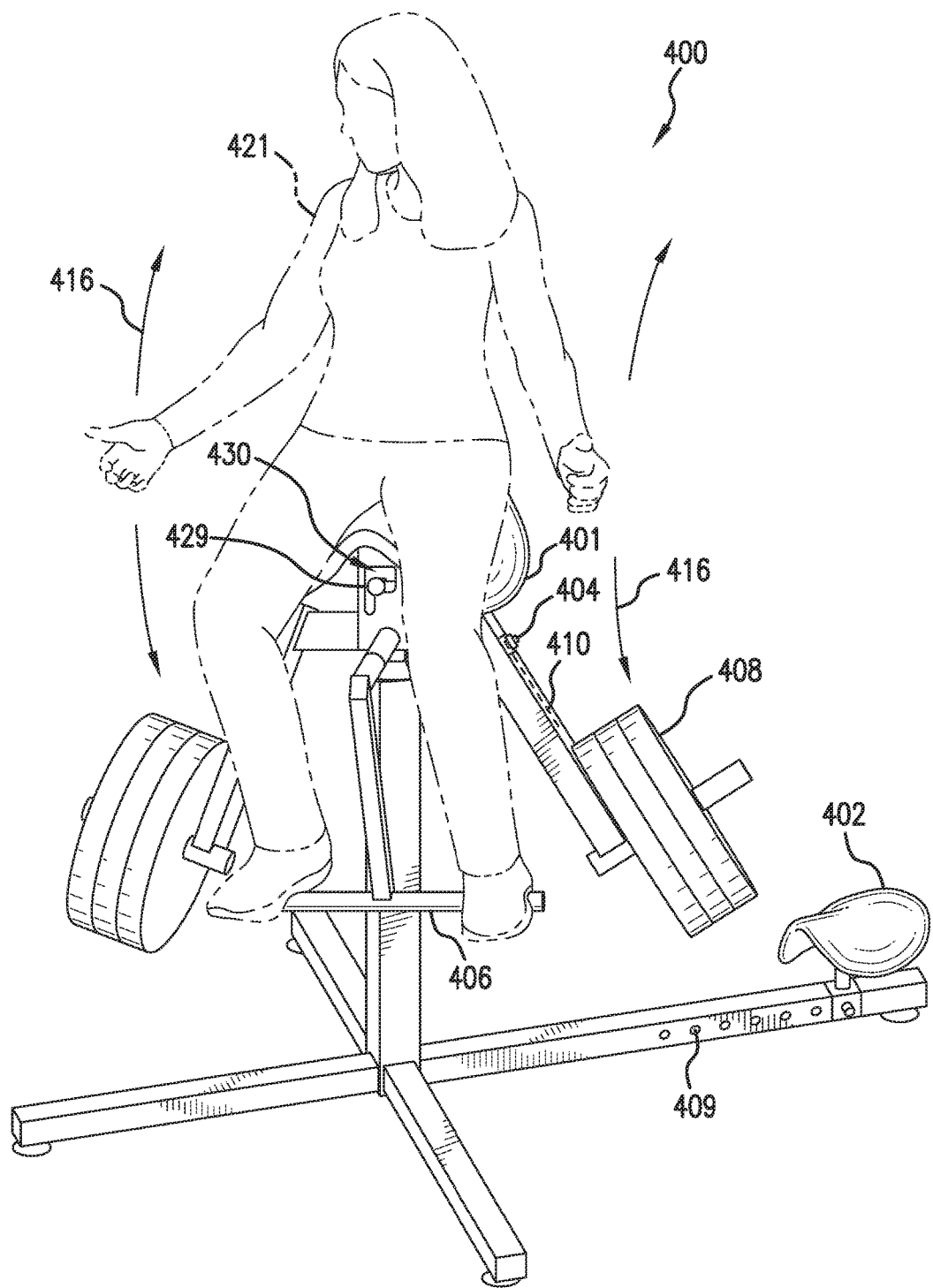
FIG. 4A is a perspective view of the illustrative core training apparatus which depicts a third operational mode.
Figure 4B:
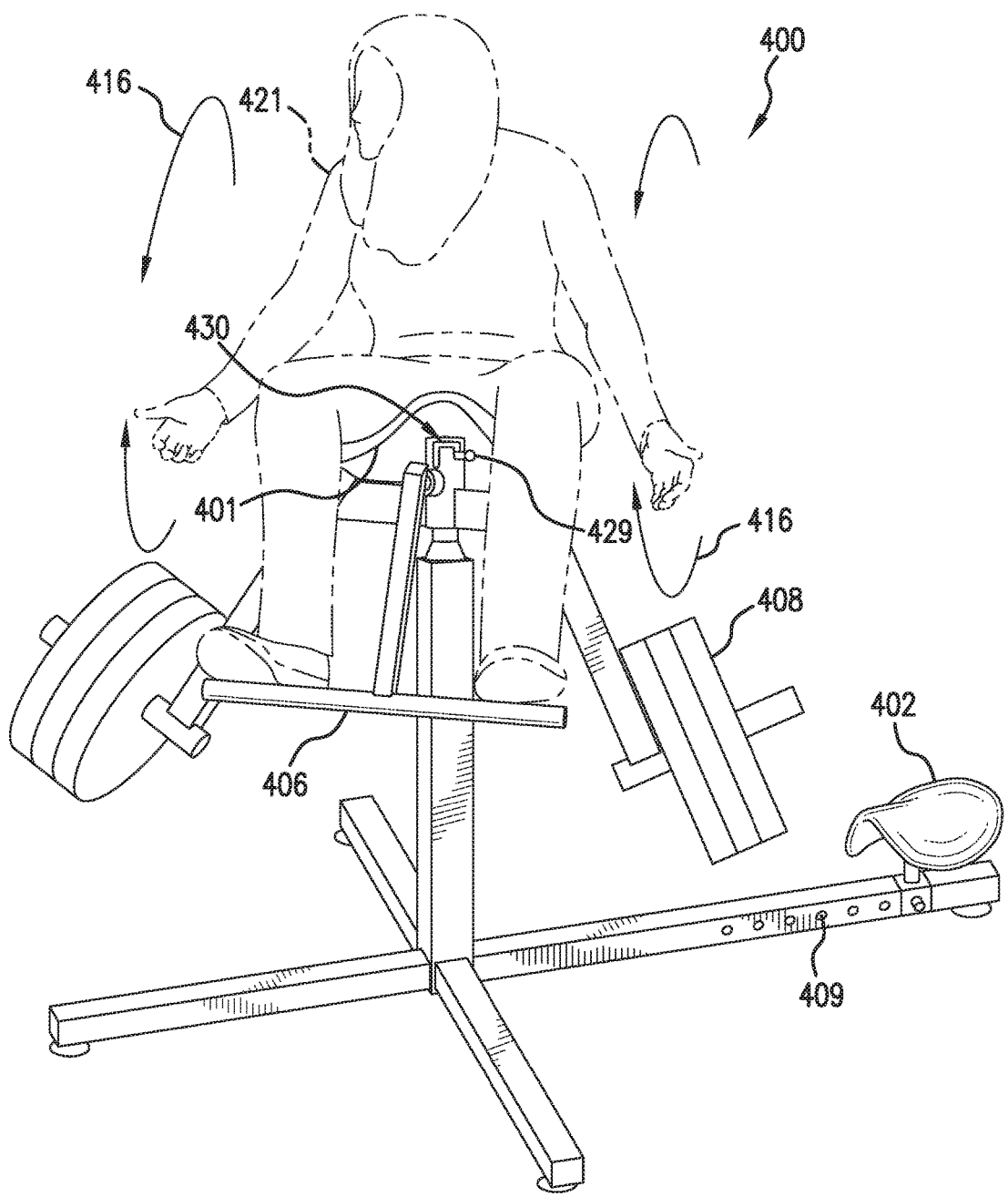
FIG. 4B is a perspective view of the illustrative core training apparatus which further depicts the third operational mode.

FIGS. 4A-4B show another operational mode in which a user sits atop the seat 401 and articulates the arm assembly through use of her core muscles. In this embodiment the handlebar/footrest 406 is secured into a lower position and the user's feet rest on the footrest 406. The user pivots her upper torso relative to her lower torso in order to articulate the apparatus in a front-to-back motion illustrated by arrows 416. FIG. 4A illustrates a point in the range of motion in which the apparatus is articulated to the front (taking the user as the frame of reference). FIG. 4B illustrates a point in the range of motion in which the apparatus is articulated to the rear (again, taking the user as the frame of reference).

Figure 5:
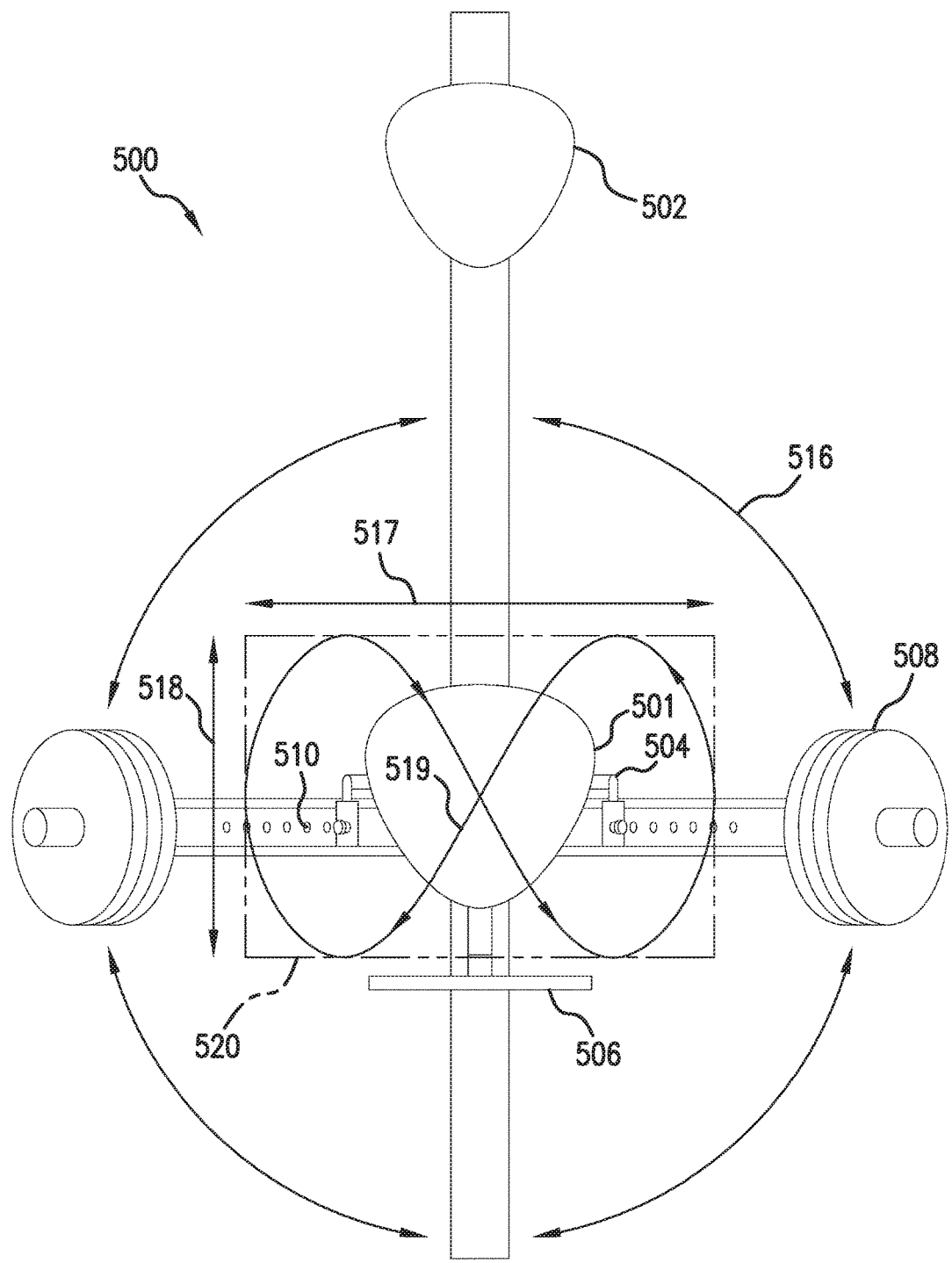
FIG. 5 is a plan view of an illustrative core training apparatus which depicts various operational modes.

FIG. 5 is a plan view of the core training apparatus 500 which shows various alternative exercise motions similar to those illustrated in FIGS. 3 and 4. As an alternative to or in addition to the side-to-side and front-to-back motions shown in FIGS. 3 and 4, the user may articulate the apparatus through a figure eight motion 519. By way of example and not limitation, the user can also articulate the apparatus in a rectangular pattern 517/518 wherein the apparatus is not permitted to return to the center position but instead the apparatus is articulated along the outline of rectangle 520. The apparatus may also be articulated in a circular pattern 516, during which the apparatus is likewise not permitted to return to the center or neutral position (shown in FIG. 1) during the exercise.

Figure 6:
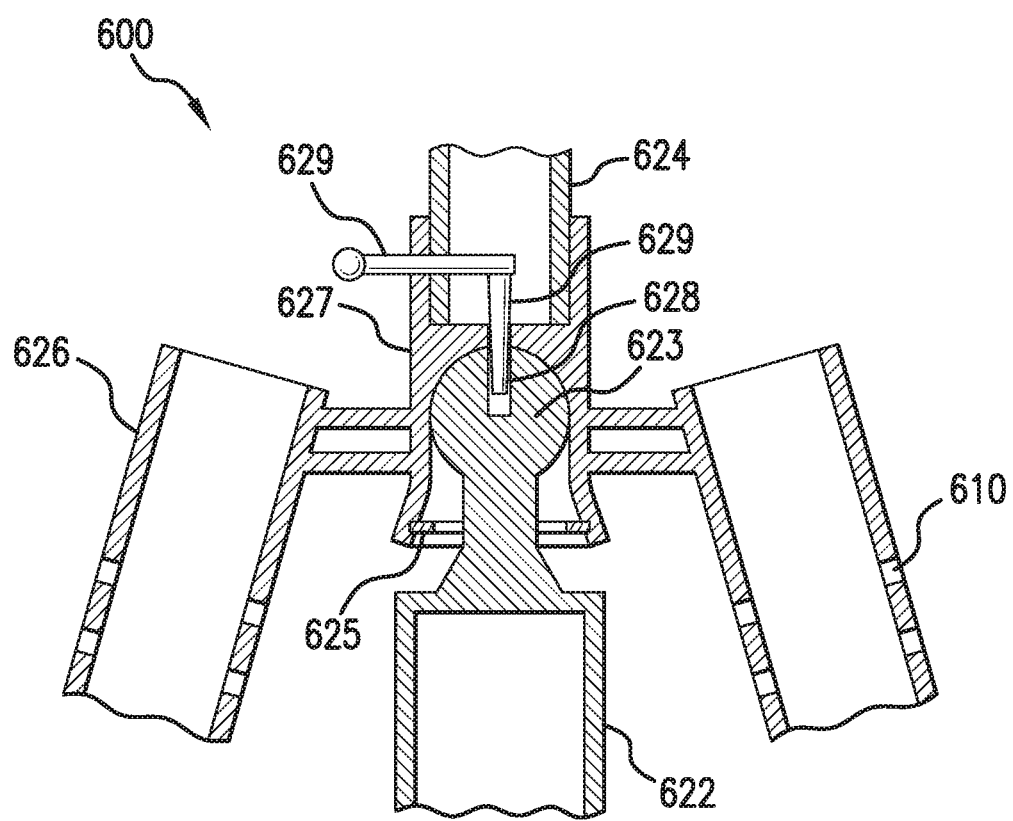
FIG. 6 is a front cross-sectional view of an exemplary angular coupling system in an illustrative core training apparatus.

FIG. 6 is a front cross-sectional view of an exemplary angular coupling system in an illustrative core training apparatus. An exemplary angular coupling system 600 for use in various embodiments of the core trainer and/or the row trainer includes a rigid support base member 622 having at a top end a ball 623. Movably coupled to the ball member 623 is a socket member 627, with a cup-shaped aperture to receive the ball member 623. The socket member is adapted to deflect around three orthogonal axes, for example, or other three-dimensional coordinate axes, defined with respect to the ball 623. This motion can be restricted when a locking pin 629 is positioned in a locking channel 628 in the ball 623. The locking pin 629 position is controlled by a user-accessible lever. When retracted up so that the pin is clear of the locking channel 628, then relative movement of the socket member 627 relative to the ball 623 is not restricted by the pin 629. The user manipulation of the lever is guided by an L-shaped locking pin slot 130, as shown, for example, with reference to FIGS. 1-2.

The socket member is coupled to an actuating member 624, examples of which are described with reference to a center post with reference to FIG. 1. In the depicted example, laterally extending members 626 that support ballast (not shown) are integrally connected to the socket member 627.

In the depicted example, the socket member 627 receives a removable annular retaining ring 625 adjacent the opening of the aperture and proximate a neck region just below and supporting the ball 623 on the rigid base member 622. The retaining ring 625 has an inner diameter slightly less than an outer diameter of the ball 623 to prevent the socket member 627 from inadvertently decoupling from the ball 623, for example, during ballast changes, exercise, and mounting or dismounting operations.

Figure 7:
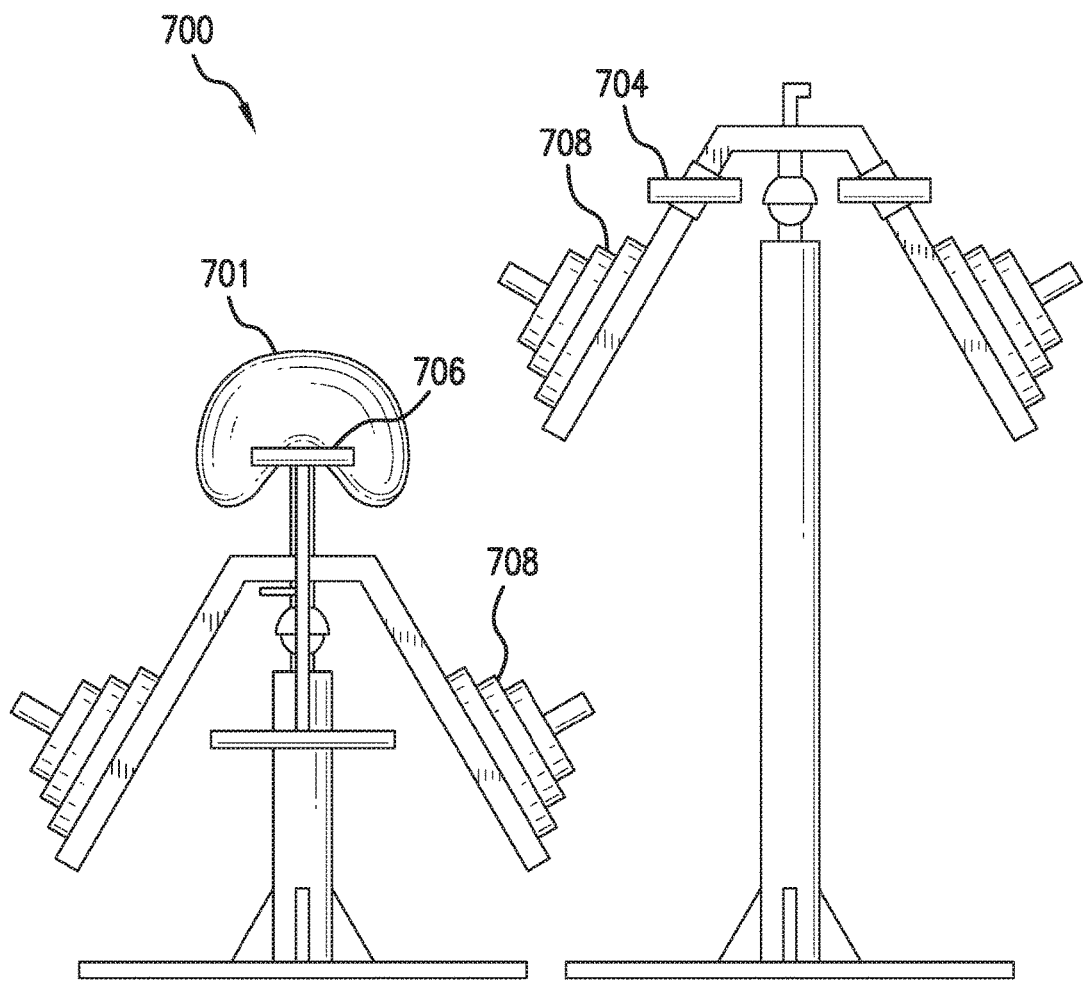
FIGS. 7, 8 and 9 are front and side views of illustrative core training apparatus with illustrative row training apparatus.
Figure 8:
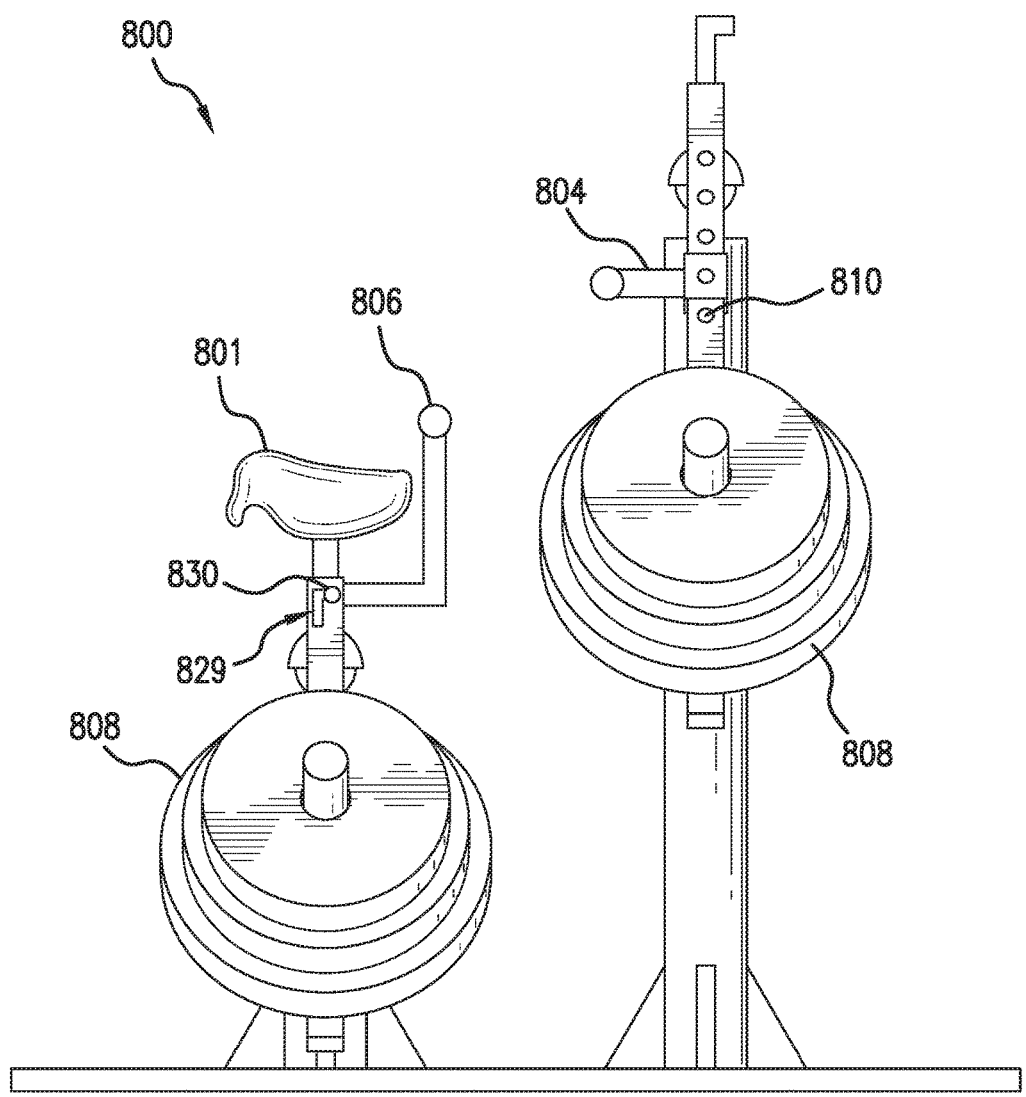
Figure 9:
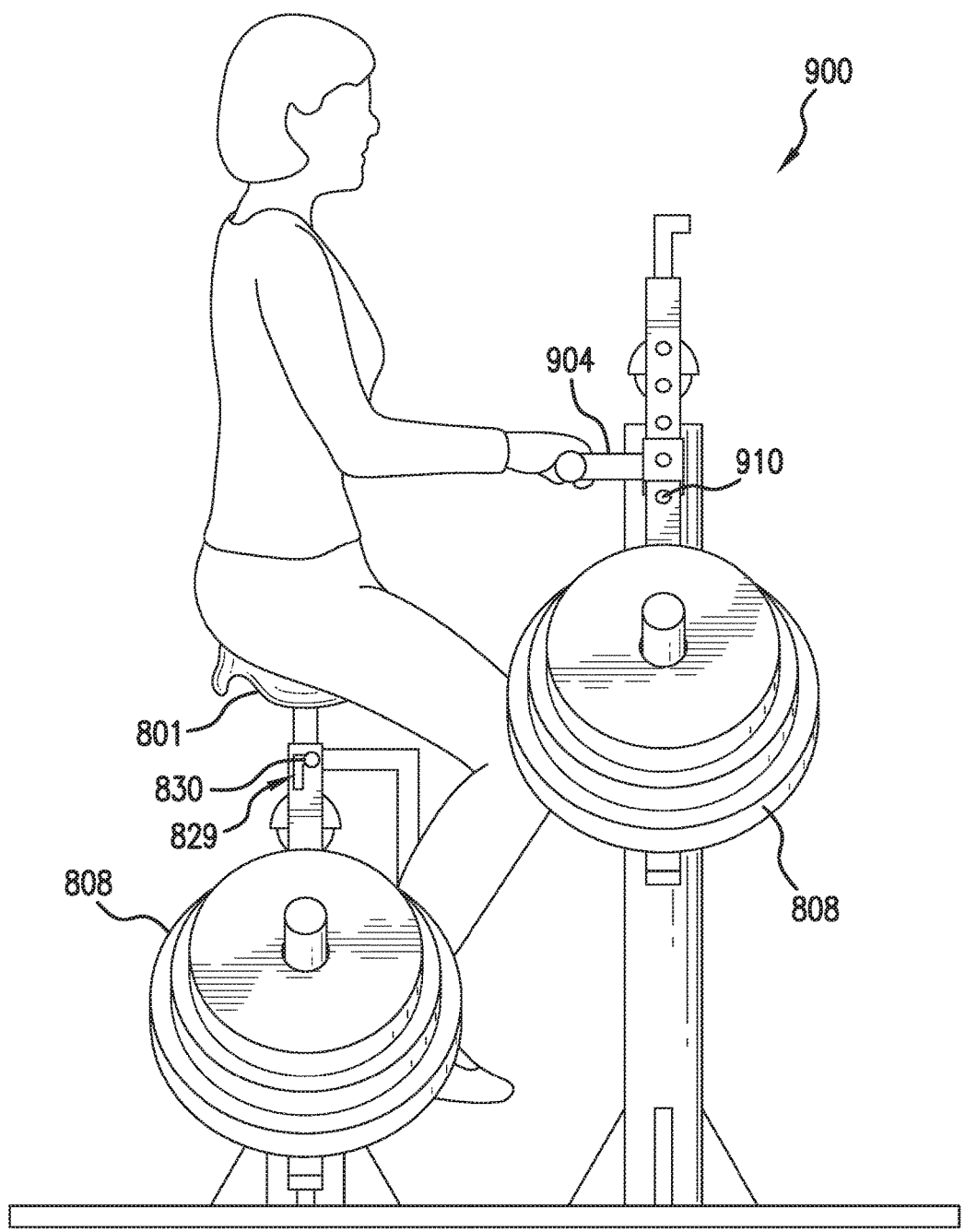

FIGS. 7, 8, and 9 are front and side views of illustrative core training apparatus with illustrative row training apparatus. As depicted in FIG. 7, an exemplary exercise system includes a core trainer and a row trainer. The core trainer includes a seat 701 for a human user, and a dual handrest/footrest 706. Supported by an articulating assembly movably coupled to a ball joint are the seat 701 and opposing ballasts 708, which may provide controlled amounts of inertia and/or gravitational weight. In operation, the user exercises core muscles to impart motion profiles to the articulating assembly of the core trainer.

The row trainer as depicted includes an articulating rowing assembly movably coupled to a ball joint and opposing ballasts 708, which may provide controlled amounts of inertia and/or gravitational weight. In operation, the user grasps handles 704 and pulls and pushes to exercise, for example, upper body and/or core muscles to impart motion profiles to the articulating assembly of the row trainer.

FIG. 8 shows an exemplary exercise system with a locking pin 829 and locking pin slot 830 accessible from under the seat 801 on the right side of a user when seated on the seat 801. The pin 830 is shown in an upward retracted state, which corresponds to an unlocked state of the ball-and-socket. In this depicted example, the handrest 806 is positioned in an upper position for easy grasping by the user.

In the depicted example, the ballast of the core trainer is supported on posts that are coupled to opposing laterally extending members of a fixed length. In some other embodiments, the length of the laterally extending members may be adjustable.

The row trainer is positioned in front of the user seated on the seat 801, with handles 804 within reach of the user seated on the seat 801. By applying force via the handles 804, the user may cause motion of the articulating assembly that supports the ballast 808 on the row trainer. In this depicted example, the row trainer includes adjustable laterally extending members along which the user can adjust the handles 804. By adjusting the handles down, the user can select a wider separation between the left and right handles 804, for example. This adjustable separation of the handles 804 may advantageously accommodate different exercises and a range of user body sizes.

FIG. 9 illustrates an exemplary user seated on the core trainer and grasping the row trainer. The user has positioned the handrest/footrest 806 into a lower position for use as a footrest.

On the top of the row trainer is an L-shaped lever coupled to a locking pin for immobilizing the ball-and-socket on the row trainer, for example, during ballast changes. In the retracted state (as shown) the articulating assembly on the row trainer is free to be used for exercise. When rotated to be inserted into a locking channel in the ball, the row trainer articulating assembly may be locked. Examples of this operation are described in further detail with reference to FIG. 6.

Figure 10:
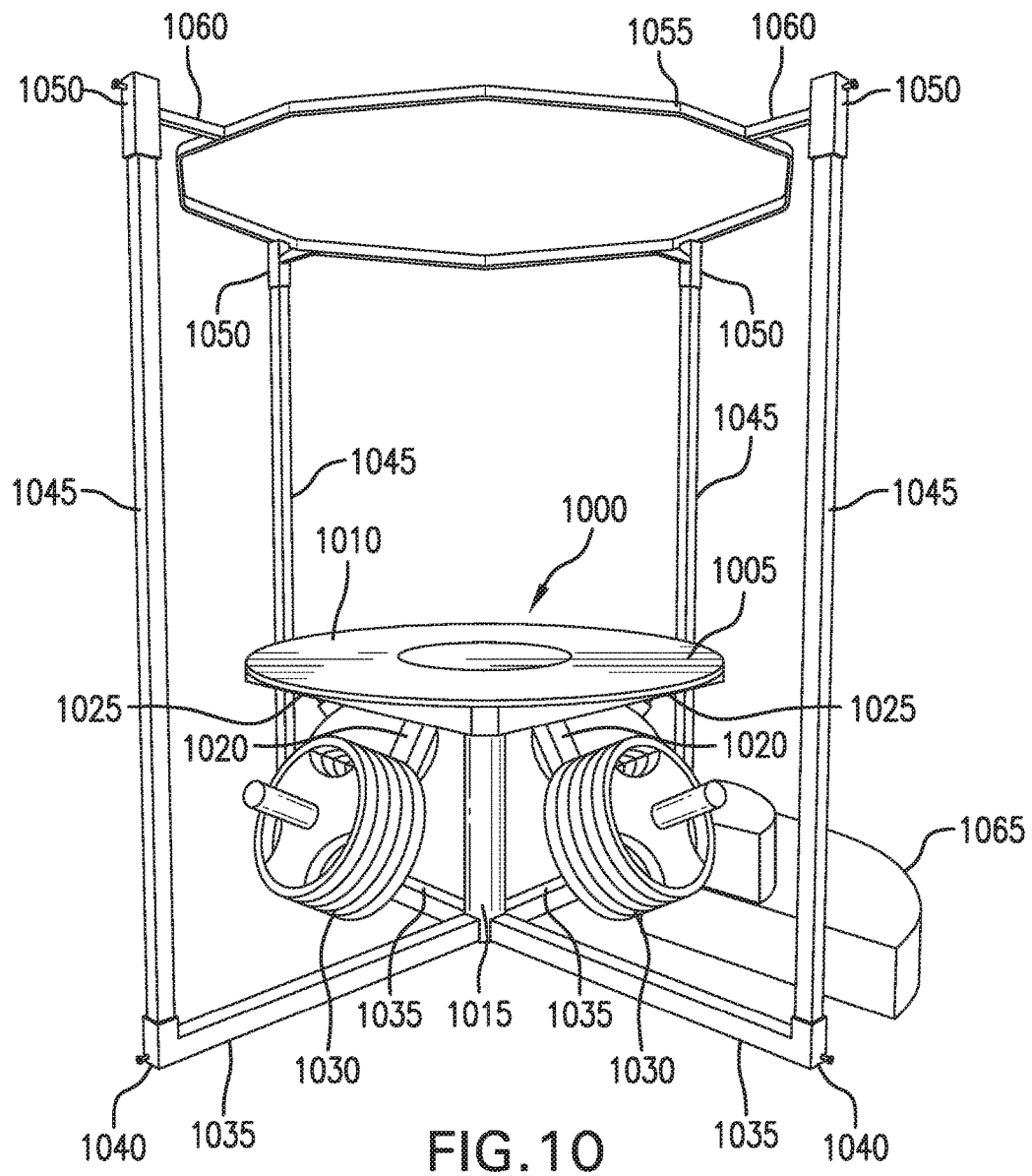
FIG. 10 depicts a perspective view of a safety cage for an exemplary board trainer.

FIG. 10 depicts a perspective view of a safety cage for an exemplary balance trainer. A balance trainer 1000 includes a platform 1005 having a substantially planar upper surface 1010. The substantially planar upper surface 1010 may receive a person in a standing position. Such a substantially planar upper surface has been described in, for example, at least page 9 of the drawings, U.S. Provisional Application Ser. No. 61/760,832 entitled "Core Exercise Apparatus and Methods," filed by Byron Tietjen, et al., on Feb. 5, 2013, the entire contents of which are hereby incorporated by reference. The platform 1005 attaches to a pedestal 1015 via a ball and socket joint (not shown). A set of L-shaped arms 1020 laterally extend from a lower surface 1025 of the platform 1005 to receive and retain ballast plates, for example, in a position substantially laterally offset from the pedestal 1015 when the platform 1005 is in a centered position. The set of L-shaped arms 1020 may stabilize the platform 1005 because the set of L-shaped arms 1020 lowers the center of mass of the platform 1005. Weighted plates 1030 slidably engage the set of L-shaped arms 1020 via an aperture. A set of base members 1035 extend from the pedestal 1015 to a distal end 1040 outside the periphery of the platform 1005. A support member 1045 extends substantially orthogonal to the base members 1035 from each distal end 1040.

The support members 1045 extend above the platform 1005 to a support distal end 1050. A handrail 1055 connects to the support members 1045 via handrail support brackets 1060. The handrail 1055 may function such that a user may use the handrail 1055 for assisted balancing while standing on the platform 1005. The support members 1045 may be telescopic to adjust the height of the handrail 1055 in accordance with the height of a user, for example. In some embodiments, the handrail 1055 may be triangular to allow a user to lean on the handrail 1055. A step member 1065 releasably attaches to one of the base members 1035 such that the user may use the step member 1065 to mount the balance trainer 1000.

Figure 11:
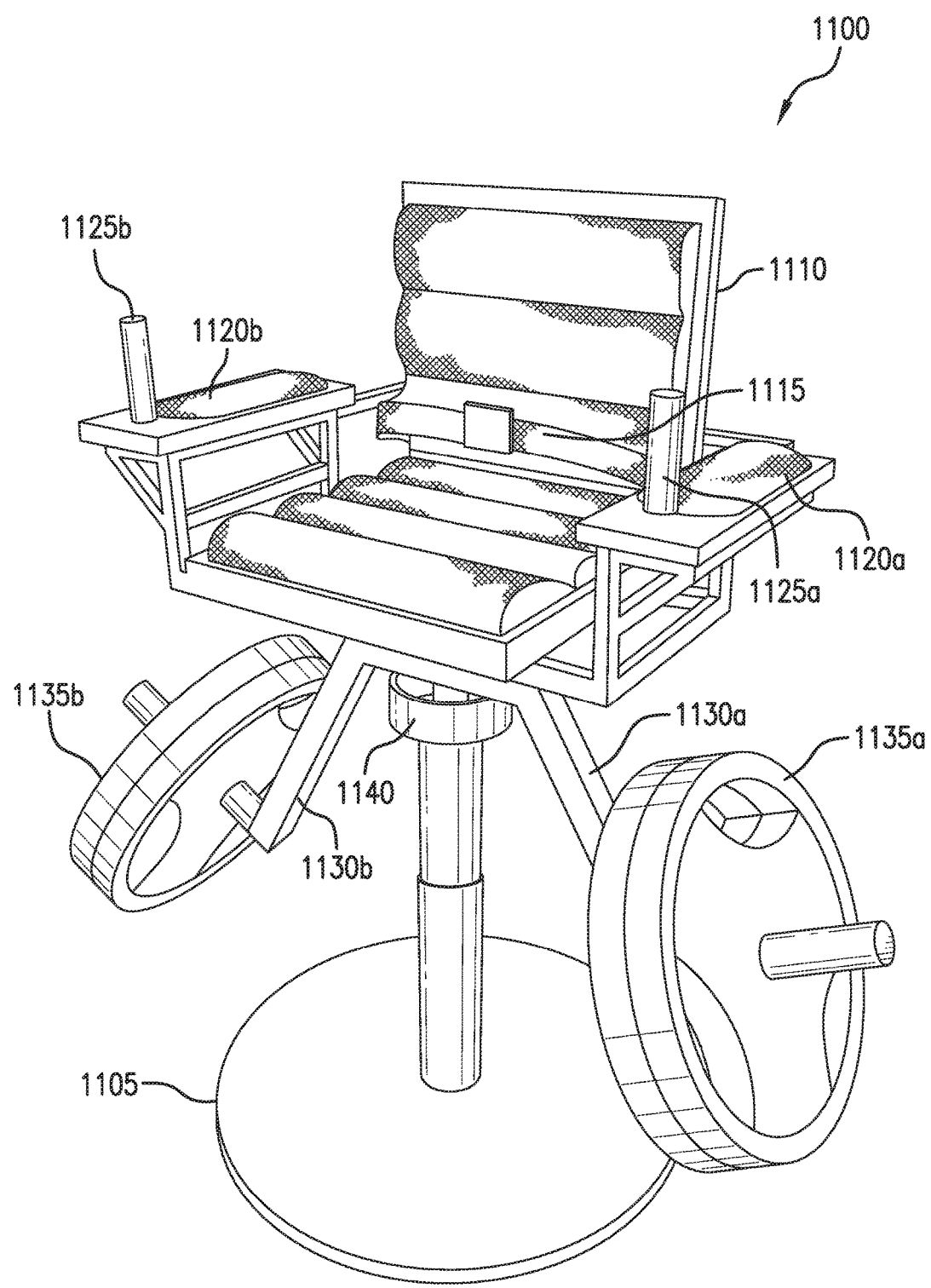
FIG. 11 depicts a perspective view of an exemplary core trainer having a seat.

FIG. 11 depicts a perspective view of an exemplary core trainer having a seat. A seated core trainer 1100 includes a base 1105. A seat 1110 includes a securing strap 1115. The seat 1110 pivotally connects to the base 1105 via a ball-and-socket joint (not shown). Such a ball-and-socket joint has been described, for example, in at least at FIG. 6 of U.S. application Ser. No. 14/173,606 entitled "Core Exercise Apparatus and Methods," filed by Terri Todd, et al., on Feb. 5, 2014, the entire contents of which are hereby incorporated by reference. The seat 1110 includes a pair of arm rests 1120a, 1120b. Each pair of arm rests 1120a, 1120b includes a hand grip 1125a, 1125b. A user may use the hand grips 1125a, 1125b to maintain a desired position while sitting on the seat 1110. The strap 1115 may further secure the user while sitting on the seat 1110. A pair of L-shaped arms 1130a, 1130b laterally extend from below the seat 1110 to receive and retain ballast plates, for example, in a position substantially laterally offset from the pedestal 1015 when the platform 1005 is in a centered position. As depicted, two weighted plates 1135a, 1135b (e.g., ballast plates) slidably mount on each L-shaped arm 1130a, 1130b. Weighted plates, such as the weighted plates 1135a, 1135b, may be added or removed to adjust the stability of the seated core trainer 1100. A safety collar 1140 (described below in further detail) mounts below the seat 1110. With reference to FIG. 10, the seat 1110 may provide a more stable platform than the platform 1005, for example. The seat 1110 may permit a user, such as a wheelchair-bound user, for example, to use the seated core trainer 1100 to exercise the core of the user.

Figure 12:
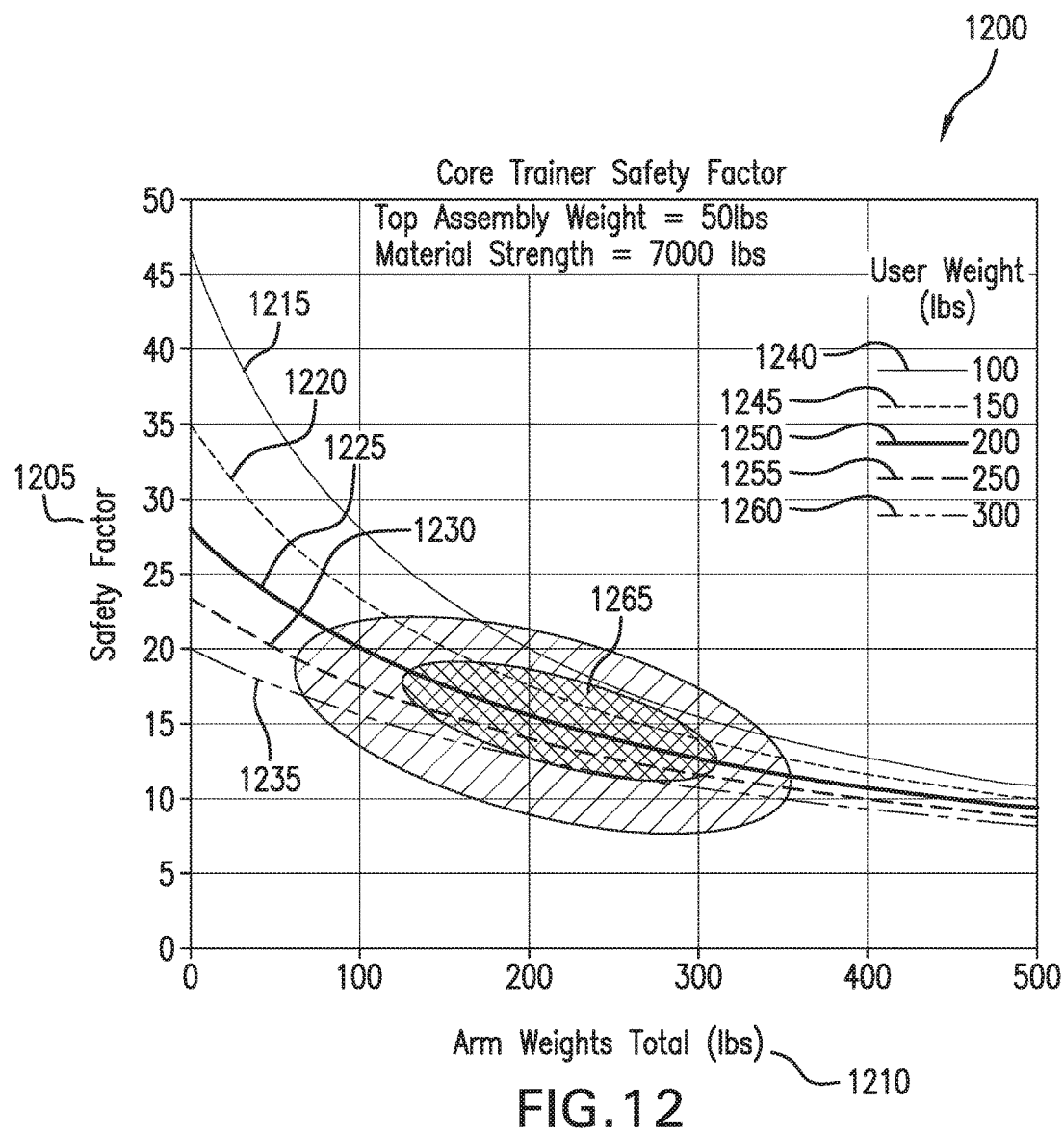
FIG. 12 depicts a graph illustrating a safety factor for an exemplary core trainer.

FIG. 12 depicts a graph illustrating a safety factor for an exemplary core trainer. A graph 1200 illustrates an equipment mechanical safety factor 1205 as it relates to a weight total 1210 of weighted plates slidably mounted on L-shaped arms, such as the weighted plates 1135a, 1135b slidably mounted on the L-shaped arms 1130a, 1130b, with reference to FIG. 11. As depicted, the graph 1200 illustrates a material strength of 7000 lbs. and a top assembly weight of 50 lbs. In the event the material strength or the top assembly weight changes, the graph 1200 may be adjusted to reflect the changes.

Each plot 1215-1235 corresponds to a user weight 1240-1260, respectively. A first shaded area 1265 of the graph 1200 illustrates a range of values associated with typical ranges of the weight total 1210 and the user weight 1240-1260. As depicted, the plots 1215-1235 remain above an equipment mechanical safety factor 1205 of 9. In an illustrative example, equipment mechanical safety factor above 9 indicate a reliable and low maintenance device.

Figure 13:
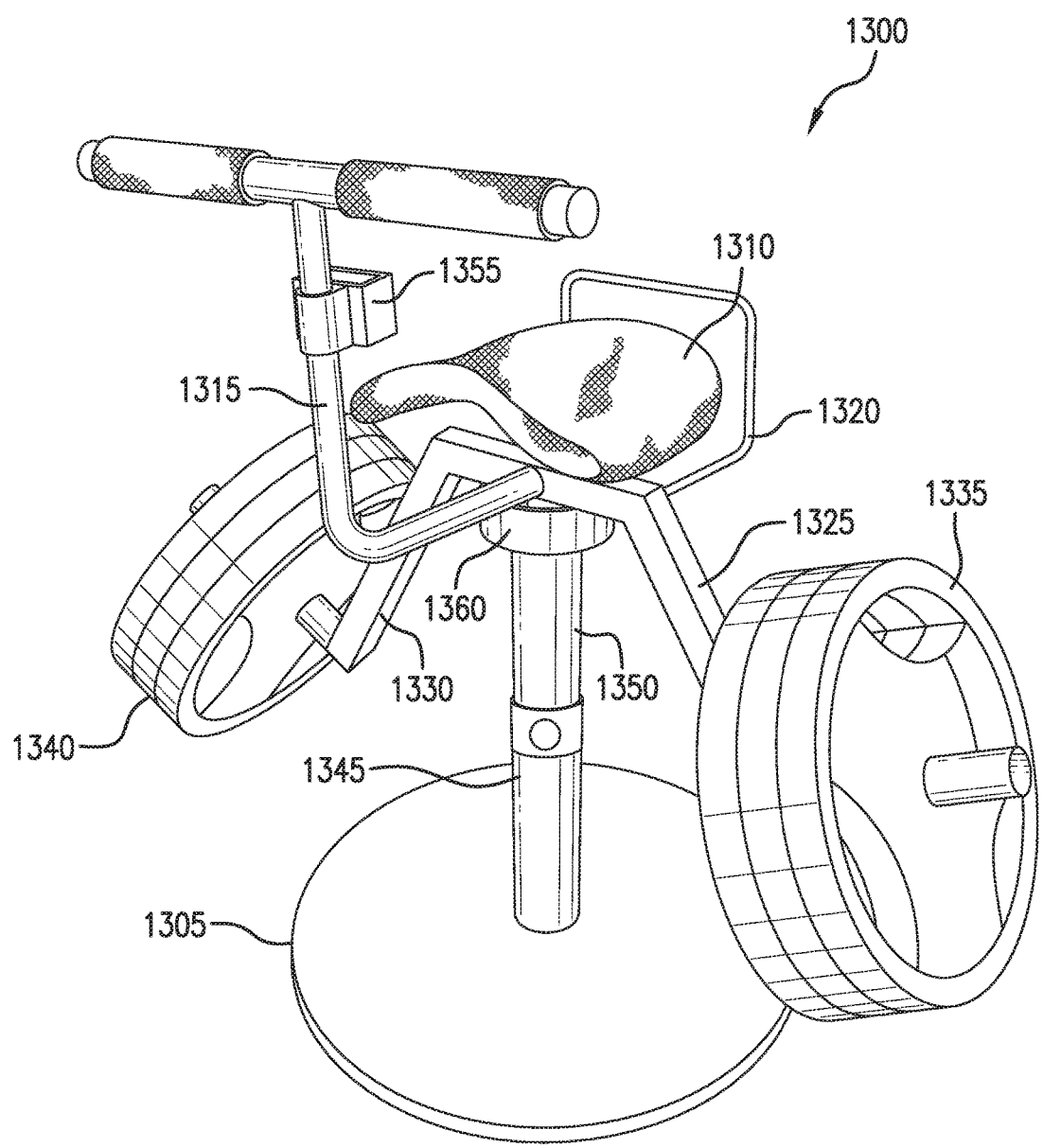
FIG. 13 depicts a perspective view of an exemplary core trainer.

FIG. 13 depicts a perspective view of an exemplary core trainer. A core trainer 1300 includes a base 1305. A saddle-style seat 1310 pivotally mounts on the base 1305 via a ball-and-socket joint (not shown). A handle 1315 extends from underneath the saddle-style seat 1310 and upwards to provide a handle 1315 such that a user seated on the saddle-style seat 1310 may grip the handle 1315. A user may use the handle 1315 to securely maintain a desired position while operating the core trainer 1300. A safety bar 1320 extends from underneath the saddle-style seat 1310 and in an opposite direction from the handle 1315. The safety bar 1320 may provide a user security against sliding off the saddle-style seat 1310. A pair of L-shaped arms 1325, 1330 laterally extend from below the saddle-style seat 1310 to receive and retain ballast plates, for example, in a position substantially laterally offset from the pedestal 1015 when the platform 1005 is in a centered position. A multiple of weighted plates 1335, 1340 slidably mount on each L-shaped arm 1325, 1330, respectively.

The base 1305 includes a vertically extending lower pedestal member 1345 and a vertically extending upper pedestal member 1350. As depicted, the upper pedestal member 1350 includes a telescoping member with respect to the lower pedestal member 1345. The upper pedestal member 1350 extends from the ball joint to the lower pedestal member 1345. The upper pedestal member 1350 may adjust to accommodate persons of different heights, for example. In some embodiments, the lower pedestal member 1345 and the upper pedestal member 1350 may be formed of a unitary construction. The upper pedestal member 1350 may be available in various lengths to accommodate different height of different users. In an illustrative example, the upper pedestal member 1350 may releasably attach to the saddle-style seat 1310 at one end and to the base 1305 at an opposite end. A holder 1355 fixedly attaches to the handle 1315. The holder 1355 may receive an electronic portable device, which may provide exercise programming information, examples of which are described with reference to FIGS. 14-16. In some embodiments, the holder 1355 may releasably attach to the handle 1315. The holder 1355 may attach anywhere along the handle 1315. With reference to FIG. 10, the holder 1355 may releasably attach to a periphery of the platform 1005.

A safety collar 1360 mounts to the saddle-style seat 1310 between the saddle-style seat 1310 and the base 1305. The safety collar 1360 may prevent the saddle-style seat 1310 from pivoting too far in any direction. In the depicted embodiments, the safety collar 1360 mounts on an underside of the saddle-style seat 1310. The safety collar 1360 may move in conformity to the displacement of the saddle-style seat 1310. The safety collar 1360 may contact the upper pedestal member 1350 at a predetermined maximum displacement. As such, the safety collar 1360 may prevent the saddle-style seat 1310 from tipping over. A user may vertically adjust the safety collar 1360 below the saddle-style seat 1310 at a maximum position to substantially restrict pivotal displacement of the saddle-style seat 1310. For example, the safety collar 1360 may be adjusted to substantially restrict pivotal displacement during loading or unloading of ballast plates. In an illustrative example, the safety collar 1360 may decrease the predetermined maximum displacement as the safety collar 1360 is displaced towards the base 1305. An edge of the safety collar 1360 that contacts the upper pedestal member 1350 may be contoured or shaped to protect against chafing or cutting of the upper pedestal member 1350.

In some embodiments, a safety collar may mount to the upper pedestal member 1350 instead of the seat 1310. The safety collar may remain in a fixed position as the saddle-style seat pivots. The saddle-style seat 1310 may contact the safety collar to prevent the saddle-style seat 1310 from exceeding a predetermined maximum displacement. The safety collar may be shaped at a contacting edge, such as the edge of the safety collar that contacts the saddle-style seat 1310, to protect against chafing or cutting of the portion of the saddle-style seat 1310 when the saddle-style seat 1310 contacts the safety collar.

In various embodiments, a safety collar may be adapted to adjust vertically via a manual adjustment mechanism. For example, the manual adjustment mechanism may include a screw-type engagement (e.g., threaded) such that a user may vertically displace the safety collar by manually rotating the safety collar along the screw-type engagement. The safety collar may include, for example, a spring biased locking pin that engages receptacles along the screw-type engagement to lock the safety collar at a desired vertical position. In some embodiments, the manual adjustment mechanism may include an Archimedes screw with locking pins, for example.

In various embodiments, a safety collar may be adapted to adjust vertically via an automated adjustment mechanism, such as an electrically, pneumatically, or hydraulically powered actuator, for example. The automated adjustment mechanism may include a motor-driven linear type actuator, for example. The linear type actuator may be housed within a pedestal member such as the lower pedestal member 1345, for example. The linear type actuator may include a threaded surface that engages the safety collar. In response to the linear type actuator rotating the threaded surface, the safety collar may vertically displace along the pedestal member. The automated adjustment mechanism may be controlled by the user accessing an app on the mobile device or an electronic switch on the handle 315, for example. In some embodiments, a user may control the automated adjustment mechanism via a mechanical lever.

Figure 14:
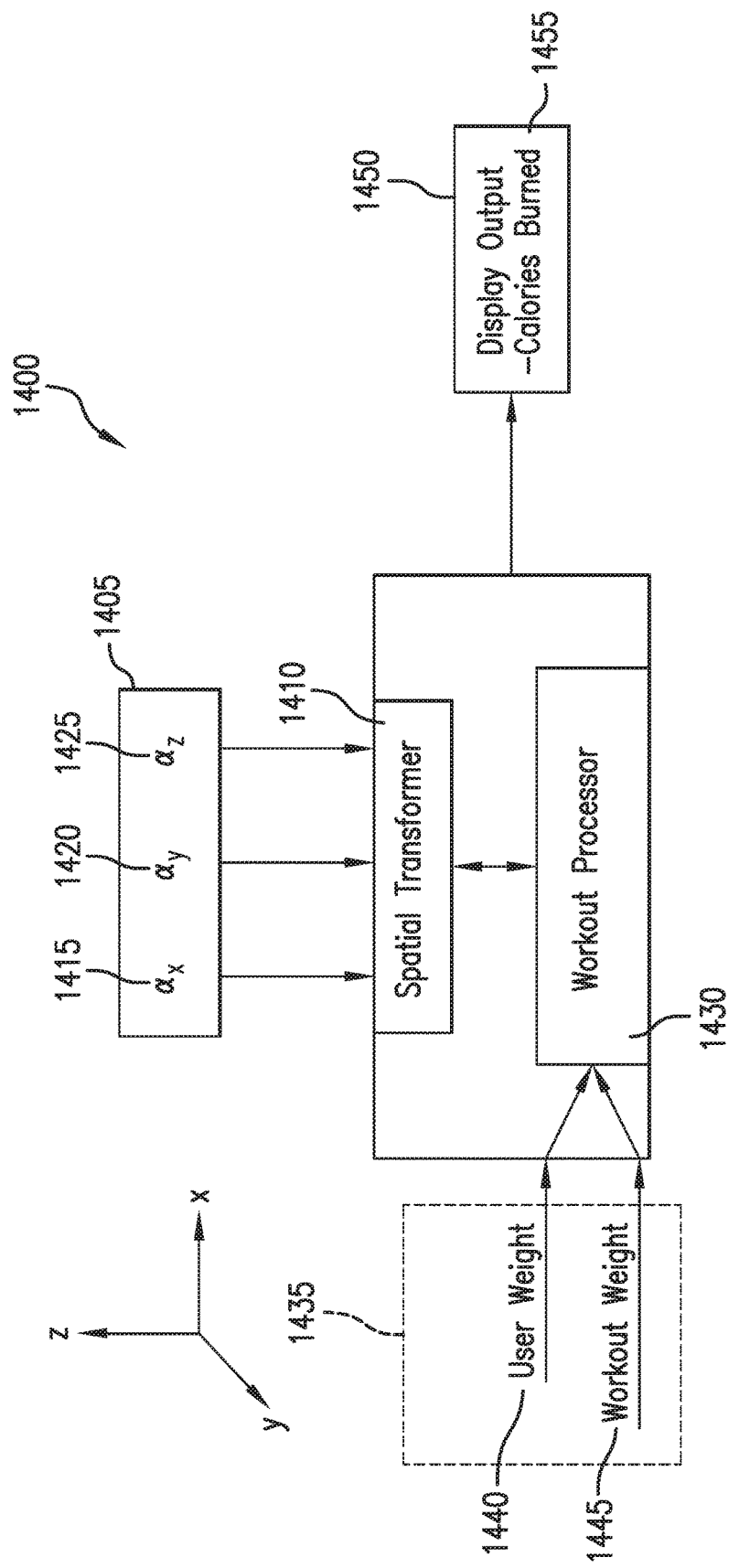
FIG. 14 depicts a block diagram illustrating an exemplary trainer processor.

FIG. 14 depicts a block diagram illustrating an exemplary trainer processor. A trainer processor 1400 receives motion trajectory data 1405 via a spatial transformer 1410. In various embodiments, a trainer controller may monitor trajectory of one or more exercises using, for example, the balance trainer 100 or the core trainer 1300. The motion trajectory data 1405 includes an X trajectory 1415, a Y trajectory 1420, and a Z trajectory 1425. The trajectories 1415-1425 may indicate movement within three-dimensional space. In some examples, accelerometers may provide the trajectories 1415-1425. In an illustrative example, a reference position (e.g., the holder 1355) relative to a pivot point of the ball-and-socket joint may define an initial position from which the accelerometers measure the trajectories 1415-1425.

In response to the spatial transformer 1410 receiving the motion trajectory data 1405, the spatial transformer 1410 provides a displacement output in accordance with the received motion trajectory data 1405 to a workout processor 1430. In various embodiments, the displacement output may represent the motion trajectory data 1405 such that a user may determine the actual range of motion of a core trainer, for example. The user may monitor proper usage of the core trainer based on the actual range of motion. The workout processor 1430 receives pre-workout data 1435. The pre-workout data 1435 includes a user weight 1440 and a workout weight 1445 of the ballast weight loaded on the core trainer, for example. In response to receiving an output from the spatial transformer 1410 and the pre-workout data 1435, the workout processor 1430 determines a display output 1450. As depicted, the display output 1450 includes an estimate of calories burned 1455 as calculated as a function of the motion trajectory data 1405 and the pre-workout data 1435.

The motion trajectory data 1405 may be provided by accelerometers in a portable electronic device that is held by the holder 1355, for example. With reference to FIG. 13, an initial position may be determined based on the electronic portable device engaged within the holder 1355. The workout processor 1430 may determine whether a cycle associated with the predetermined motion trajectory profile is completed (discussed in further detail below) based on the initial position and the displacement output received from the spatial transformer 1410. In some embodiments, the display output 1450 may display on an electrical portable device via an app. The pre-workout data may include parameters specific to a user, such as, for example, gender and age. The workout processor 1430 may provide more accurate outputs in response to additional user-specific parameters, for example.

Figure 15A:
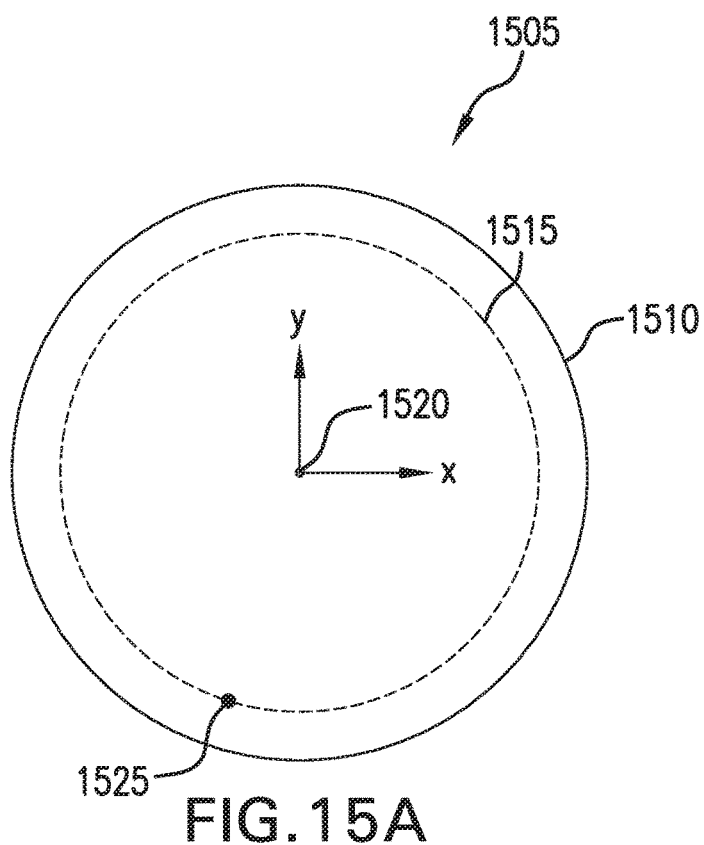
FIG. 15A depicts a top view visual representation of an exemplary circular displacement trajectory of a core trainer.

FIG. 15A depicts a top view visual representation of an exemplary circular displacement trajectory of a core trainer. A circular displacement visual representation 1505 includes an outer circle 1510 and an inner circle 1515. Both circles 1510, 1515 share a center point 1520. In an illustrative example, the center point 1520 may indicate a neutral position of a reference point on the core trainer. The outer circle 1510 represents a circular trajectory of the reference point of a core trainer. For example, with reference to FIG. 13, the outer circle 1510 may represent a circular trajectory of a reference point on the handle 1315 about the center point 1520. The inner circle 1515 may represent a circular trajectory of the holder 1355, for example.

The inner circle 1515 is traced by a reference point 1525. With reference to FIG. 14, the workout processor 1430 may determine displacements of the reference point 1525 along the X trajectory 1415 and the Y trajectory 1420. In an illustrative example, the inner circle 1515 indicates displacement of the reference point 1525 along the X trajectory 1415 and the Y trajectory 1420. The workout processor 1430 may determine that a point (e.g., position of the holder 1355) has traveled the full outer circle 1510 by measuring a total displacement of the X trajectory 1415 and the Y trajectory 1420, and comparing the total displacement to the reference point 1525.

Figure 15B:
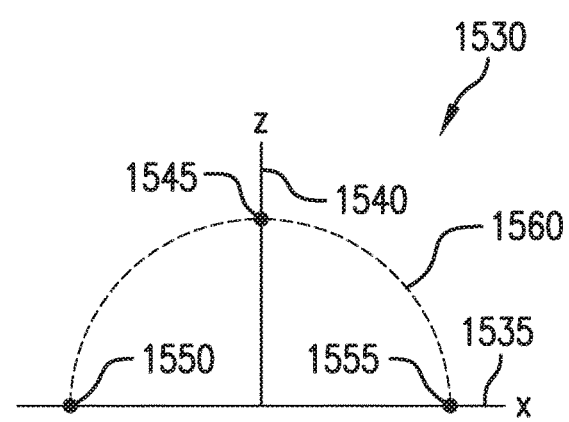
FIG. 15B depicts a side perspective view visual representation of an exemplary lateral vertical displacement trajectory of a core trainer.

FIG. 15B depicts a side perspective view visual representation of an exemplary lateral vertical displacement trajectory of a core trainer. A lateral displacement visual representation 1530 includes an X-axis 1535 and a (vertical) Z-axis 1540, such as the X-axis and Z-axis depicted in FIG. 14. As depicted, a reference point 1545 illustrates a neutral position of a predetermined point of a core trainer, such as a position of the holder 1355 before operation of the core trainer, for example. A first maximum point 1550 represents a maximum displacement along the X-axis 1535 and the Z-axis 1540. A second maximum point 1555 illustrates a maximum displacement along the X-axis 1535 and the Z-axis 1540 in a direction opposite the first maximum point 1550 along the X-axis 1535. A trajectory 1560 illustrates a range of motion for the reference point 1545.

With reference to FIG. 14, the workout processor 1430 may receive multiple plot points representing a lateral displacement of a core trainer. In an illustrative example, a predetermined motion trajectory profile may include a complete range of plot points between the first plot point 1550 and the second plot point 1555. The workout processor 1430 may determine whether a user has completed a predetermined periodic cycle, for example, by evaluating the Y-trajectory 1420 portion of the motion trajectory data 1405.

Figure 16:
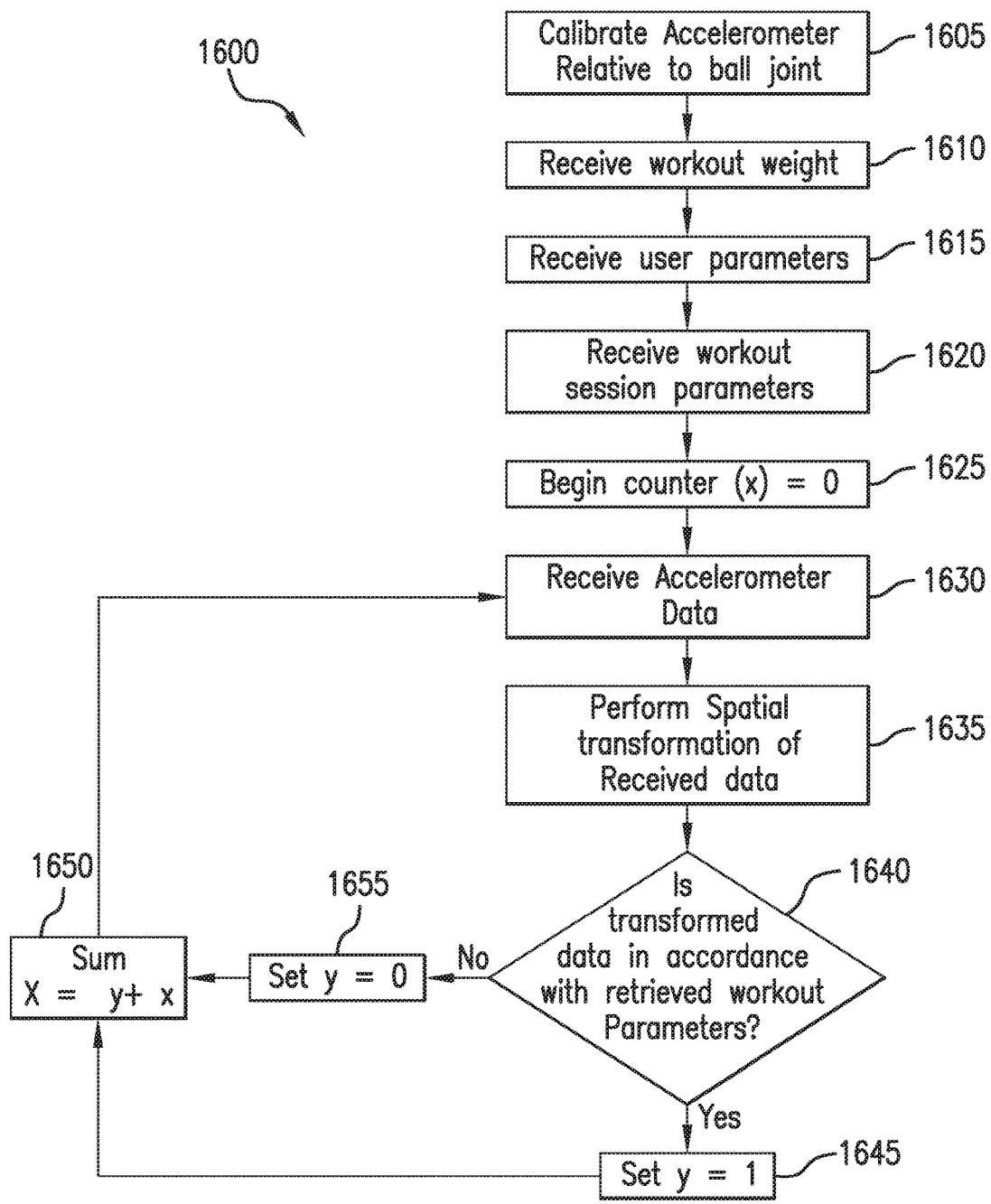
FIG. 16 depicts a flowchart of a sequence of steps for periodic motion tracking using an exemplary trainer controller.

FIG. 16 depicts a flowchart of a sequence of steps for periodic motion tracking using an exemplary trainer controller. In various embodiments, a trainer controller may monitor a trajectory of one or more exercises using, for example, the balance trainer 100 or the core trainer 1300. With reference to FIGS. 13 and 14, a sequence 1600 initiates, at 1605, when the workout processor calibrates an accelerometer relative to the ball-and-socket joint of the core trainer 1300. An electronic portable device mounted on the holder 1355 may provide the accelerometer, for example. The workout processor 1430 receives, at 1610, a workout weight (e.g., total weight for the weighted plates 1335, 1340). At 1615, the workout processor 1430 receives user parameters, such as the user weight 1440, for example.

The workout processor 1430 retrieves, at 1620, workout session parameters from a data store operatively coupled with the workout processor 1430. With reference to FIGS. 15A and 15B, the workout session parameters may include displacement ranges along the X-trajectory 1415, the Y-trajectory 1420 and Z-trajectory 1425 that define a periodic cycle. Further, the retrieved workout parameters may include a predetermined number of periodic cycles to be completed. In some embodiments, a user may transmit the workout session parameters to the workout processor 1430. The workout processor 1430 may retrieve the workout session parameters from non-volatile memory, for example. At 1625, the workout processor begins a counter by setting a first variable (e.g., x) equal to zero.

In an illustrative example, a user begins a workout session. In response to the workout session, the spatial transformer 1410 receives, at 1630, motion trajectory data. At 1635, the spatial transformer 1410 transforms the received motion trajectory data 1405 into displacement output to transmit to the workout processor 1430. The workout processor 1430 determines, at 1640, whether the displacement output matches the retrieved workout parameters. In an illustrative example, the retrieved workout parameters define a predetermined motion trajectory profile based on the X-trajectory 1415, the Y-trajectory 1420 and Z-trajectory 1425. If, at 1640, the workout processor 1430 determines that the user is matching at least the actual motion of the core trainer, for example, to be within a predetermined range of the predetermined motion trajectory profile, then the workout processor 1430 sets a second variable (y) equal to one. At 1650, the workout processor 1430 sums the current first variable (x) and the second variable (y) to calculate a new first variable (x). The workout processor 1430 then repeats step 1630 with the new first variable (x) becoming the current first variable (x).

If, at 1640, the workout processor 1430 determines the displacement output does not match the retrieved workout parameters, then the workout processor 1430 sets the second variable (y) equal to zero. At 1650, the workout processor 1430 sums the current first variable (x) and the second variable (y) to calculate a new first variable (x). The workout processor 1430 then repeats step 1630 with the new first variable (x) becoming the current first variable (x). In an illustrative example, the retrieved workout parameters may include a predetermined number of periodic cycles to be completed. The predetermined number of periodic cycles may be set by the user via an electronic portable device. In some embodiments, the electronic portable device may provide an indicator, such as a sound, for example, to indicate to a user that the predetermined number of periodic cycles is reached.

Although various embodiments have been described with reference to the figures, other embodiments are possible. For example, the handles 104 may be positioned laterally outwards of the position shown in FIG. 1. In such an embodiment, a laterally extending member couples each handle to the channel member which slideably engages the downwardly extending arms. In various embodiments the handles may be positioned approximately 2-4 feet apart, measured at the horizontal center point of each handle. In preferred embodiments the handles are approximately 2.5-3.5 feet apart, and in more preferred embodiments about 2.5 to 3 feet apart.

The horizontal offset of the handle from the downwardly extending arm may also be varied to alter the range of motion and muscles exercised. In the depicted embodiment, the handles are offset by a distance of approximately 6 inches from the centerline of the downwardly extending arms. In other embodiments, this horizontal offset is approximately 8, 10, 12, 14, 16 or 18 inches.

In various embodiments, with reference to FIG. 1, the handlebar/footrest 106 may be locked into a desired position via a locking mechanism, such a locking pin, for example. With reference to FIG. 6, the retaining ring 625 may be removed such that the socket member 627 and the ball decouple to permit greater range of movement when exercising. The ballast holding posts of FIGS. 1-5 and 7-9 may receive and retain ballast plates in a position substantially laterally offset from the rearwardly extending arm when the platform is in a centered position.

Some embodiments may provide other grip styles and/or orientations for the handles 104, for example. For example, some implementations may include multiple or variable angle grip positions for the handles 104. Some embodiments may include a flexible (e.g., rope) attachment to be grasped by the user during exercise while seated on the seat 102.

Some examples may include foot placements to receive the ball, heel, toes, and/or the entire bottom surface of the foot of the user during exercise while seated on the seat 102. By way of example, and not limitation, the foot placements may include plates with or without straps to capture the top of each foot, or a bar member extending radially from the central base support member to provide a toe hold, for example.

To aid the loading and unloading of plates 108 from the plate holding posts the center post assembly may include a downwardly extending and reciprocating pin (e.g., the locking pin 129) which engages a vertical bore in the ball member. In this way the user can articulate the pin downward to lock the arm assembly in the center or neutral position during a plate unloading or loading operation and when mounting or dismounting the apparatus. When ready to begin an exercise movement, the user can articulate the pin upwards, thereby allowing the socket to rotate freely with respect to the ball.

The angle between the downwardly extending arms and vertical support post may be, in preferred embodiments, about 10-45 degrees and in more preferred embodiments about 15-25 degrees and in the most preferred embodiments about 15-20 degrees. This angle may also be manually adjustable by a user, as shown in the provisional applications incorporated herein by reference. In such embodiments the downwardly extending arms are hingedly coupled to the center post member and pins are used to secure the arms at the desired angle.

The apparatus may also include damper elements and/or tension spring elements that extend between the vertical support posts and either or both of the downwardly extending arms and the forwardly extending arm which holds the handlebar/footrest 106. Dampers may provide increased resistance at higher rates of motion and may also prevent the apparatus from pivoting quickly, thereby reducing the risk of injury during loading/unloading or mounting/dismounting operations. Tension spring elements will tend to cause the device to return to the center or neutral position and will thereby provide a substantially modified feel and exercise for the user. Either or both of the tension springs elements or the damper elements may be configured to be toollessly removable and installable so that a user can readily remove or add spring or damper elements as desired. For instance, the ends of the spring elements and damper elements may include apertures that align with complementary apertures on flanges disposed on the downwardly extending arms and the vertical support post so that a user may readily insert pins to secure each spring or damper element in place.

Some embodiments may use flexible pivot arms having a fixed predetermined weight. The pivot arms may adjust in angle and length to adjust a counterbalance to a user on a core trainer. Such pivot arms have been described, for example, on page 5 of U.S. Provisional Application Ser. No. 61/625,098, titled "Core Balance Seat," filed by Terri Todd, et al., on Apr. 17, 2012, and, on paged 6 of U.S. Provisional Application Ser. No. 61/621,765, titled "Core Balance Seat," filed by Terri Todd, et al., on Apr. 9, 2012, and, on page 5 of U.S. Provisional Application Ser. No. 61/623,598, titled "Core Balance Seat," filed by Terri Todd, et al., on Apr. 13, 2012, and, page 9 of in U.S. Provisional Application Ser. No. 61/656,348, titled "Core Balance Seat," filed by Terri Todd, et al., on Jun. 6, 2012, the entire contents of which are incorporated herein by reference. Some embodiments may include a telescoping member in the ballast receiving arms, such as the L-shaped arms 1020 of FIG. 10, for example. The telescoping member of the ballast receiving arms may adjust a center of mass below a pivot point of a ball-and-socket joint in accordance with a user's preferences, for example. Such telescoping members have been described, for example, at least in FIG. 1 of U.S. Provisional Application Ser. No. 61/712,986, titled "Core Exercise Apparatus and Methods," filed by Byron Tietjen, et al., on Oct. 12, 2012, the entire contents of which are incorporated herein by reference.

Some embodiments may include an angular displacement sensor to detect the angular deflection of the articulating assembly, (e.g., the seat 101 or the row assembly), relative to a set of orthogonal axes defined by the articulating assembly's base member. Some embodiments may further include sensors to detect position, velocity, and/or forces associated with static or dynamic exercises. In some examples one or more sensor assemblies may operate to detect the weight of the ballast loaded on the core trainer and/or the row trainer. Various sensor outputs may be received by a central processor executing a program of instructions for recording and communicating performance metrics and other feedback to the user. By way of example, and not limitation, the processor may be configured to send audible, visual, and/or tactile feedback to the user with indicia representative of athletic performance. For example, the processor may be coupled to a display device to display a plot of instantaneous and/or historical angular deflection of the articulating assemblies of the core trainer and/or the row trainer. The processor may output real time and/or historical averages or cumulative totals of user-selected parameters, such as revolutions per minute, number of revolutions, average angular deflection, calories expended, equivalent distance rowed in a kayak, or the like, for example. In some implementations, the display may provide a programmed display of training information, such as a pre-programmed series of motion profiles with deflection plots that the user should follow. The processor may provide a score based on the user's exercise performance variance with respect to the training profile. Increasing levels of difficulty may be associated with increased angular deflections, faster velocities, alone or in combination with more taxing motion profile sequences.

The features of the foregoing embodiments can be combined as desired to achieve additional embodiments. For instance, the core chair exercise device of FIG. 9 can be modified to include the non-pivoting seat and corresponding handles of FIG. 1, such the that the user can optionally sit in this additional seat, rearward of seat 801, to execute a rowing exercise using ballast 808 while seated in a position close to the floor.

A skilled artisan will understand that the motion of the core trainer and row trainer devices described herein will be subject substantially only to the gravitational and inertial forces acting upon and through the ballast. The shear friction associated with the ball joint interface is minimal in the preferred embodiments. The effect of mass of the device itself, as opposed to the ballast, will be in most embodiments be insignificant relative to the effect of the mass of the ballast given the positioning of the ballast and the associated polar moment of inertia.

A number of embodiments have been described. Nevertheless, it will be understood that various modifications are optionally made without departing from the spirit and scope of this disclosure. Accordingly, other embodiments are within the scope of the following claims.

What is claimed is:

1. An exercise training apparatus comprising:
   a rigid base member having an upper end and a lower end;
   a pivot mechanism coupled to the upper end of the base member, the pivot mechanism comprising a ball-and-socket joint positioned along a vertical axis;
   a substantially planar platform mounted atop the pivot mechanism such that the substantially planar platform is able to freely pivot about three perpendicular axes relative to the base member, wherein the substantially planar platform is adapted to receive a user in a standing position;
   a first laterally extending member extending downwardly and in a first lateral direction relative to the ball-and-socket joint, the first laterally extending member configured to releasably receive and retain a first ballast plate in a position substantially laterally offset from the vertical axis when the platform is in a centered position; and,
   a second laterally extending member extending downwardly and in a second lateral direction relative to the ball-and-socket joint, the second laterally extending member configured to releasably receive and retain a second ballast plate in a position substantially laterally offset from the vertical axis when the first seat or platform is in a centered position,
   wherein the substantially planar platform is operable to, when in an operative exercise mode, simultaneously pivot and rotate relative to the rigid base member subject to momentum of the first ballast plate and the second ballast plate, and
   wherein a center of mass of the platform lowers below a pivot point of the ball-and-socket joint in response to the first laterally extending member and the second laterally extending member receiving and retaining the first ballast plate and the second ballast plate, respectively.

2. The exercise training apparatus of claim 1, further comprising an adjustment mechanism to adjust the height of the rigid base member such that the pivot mechanism may be disposed at various operative vertical positions.

3. The exercise training apparatus of claim 2, wherein the adjustment mechanism comprises an adjustable telescoping member.

4. The exercise training apparatus of claim 1, wherein the lower end of the base member comprises at least three base members extending substantially orthogonal relative to the upper end of the base member, each base member having a distal end that extends beyond a periphery of the platform.

5. The exercise training apparatus of claim 4, further comprising a support member extending from the distal end of each base member and substantially orthogonal relative to the at least three base members, wherein a distal end of each support member extends above the platform.

6. The exercise training apparatus of claim 5, further comprising a handrail attached to the distal end of each of the support members such that the user may grasp the handrail while standing on the platform.

7. The exercise training apparatus of claim 1, wherein the first lateral direction is generally opposite the second lateral direction.

8. The exercise training apparatus of claim 1, further comprising a third laterally extending member extending downwardly and in a third lateral direction relative to the ball-and-socket joint, the third laterally extending member configured to releasably receive and retain a third ballast plate in a position substantially laterally offset from the vertical axis when the platform is in a centered position.

9. The exercise training apparatus of claim 8, further comprising a fourth laterally extending member extending downwardly and in a fourth lateral direction relative to the ball-and-socket joint, the fourth laterally extending member configured to releasably receive and retain a fourth ballast plate in a position substantially laterally offset from the vertical axis when the platform is in a centered position.

10. The exercise training apparatus of claim 1, further comprising a safety collar mounted to the upper end of the base member to limit pivotal displacement of the substantially planar platform.

11. The exercise training apparatus of claim 1, further comprising a safety collar mounted to the substantially planar platform to limit pivotal displacement of the substantially planar platform.

12. An exercise training apparatus comprising:
    a rigid base member having an upper end and a lower end;
    a pivot mechanism coupled to the upper end of the base member, the pivot mechanism comprising a ball-and-socket joint positioned along a vertical axis;
    a substantially planar platform mounted atop the pivot mechanism such that the substantially planar platform is able to freely pivot about three perpendicular axes relative to the base member, wherein the substantially planar platform is adapted to receive a user in a standing position;
    a first laterally extending member extending downwardly and in a first lateral direction relative to the ball-and-socket joint, the first laterally extending member configured to releasably receive and retain a first ballast plate in a position substantially laterally offset from the vertical axis when the platform is in a centered position; and, a second laterally extending member extending downwardly and in a second lateral direction relative to the ball-and-socket joint, the second laterally extending member configured to releasably receive and retain a second ballast plate in a position substantially laterally offset from the vertical axis when the first seat or platform is in a centered position, wherein a center of mass of the platform lowers below a pivot point of the ball-and-socket joint in response to the first laterally extending member and the second laterally extending member receiving and retaining the first ballast plate and the second ballast plate, respectively.

13. The exercise training apparatus of claim 12, further comprising an adjustment mechanism to adjust the height of the rigid base member such that the pivot mechanism may be disposed at various operative vertical positions.

14. The exercise training apparatus of claim 12, wherein the first lateral direction is generally opposite the second lateral direction.

15. The exercise training apparatus of claim 12, further comprising a third laterally extending member extending downwardly and in a third lateral direction relative to the ball-and-socket joint, the third laterally extending member configured to releasably receive and retain a third ballast plate in a position substantially laterally offset from the vertical axis when the platform is in a centered position.

16. The exercise training apparatus of claim 15, further comprising a fourth laterally extending member extending downwardly and in a fourth lateral direction relative to the ball-and-socket joint, the fourth laterally extending member configured to releasably receive and retain a fourth ballast plate in a position substantially laterally offset from the vertical axis when the platform is in a centered position.

17. The exercise training apparatus of claim 12, further comprising a safety collar mounted to the upper end of the base member to limit pivotal displacement of the substantially planar platform.

18. The exercise training apparatus of claim 12, further comprising a safety collar mounted to the substantially planar platform to limit pivotal displacement of the substantially planar platform.

* * * * *